US009696332B2

(12) United States Patent
Brutler et al.

(10) Patent No.: US 9,696,332 B2
(45) Date of Patent: Jul. 4, 2017

(54) AUTOMATED LIQUID HANDLING DEVICE

(75) Inventors: Zoltan Brutler, Groton, MA (US);
Carl Doan, Tyngsboro, MA (US);
Erich Fournier, Hudson, NH (US); Ari Kukkonen, Helsinki (FI); Scott Leclerc, Ashby, MA (US); George Lyman, Kennebunkport, ME (US);
Colin Reynolds, Hudson, NH (US);
Thomas A. Sherwin, Newfields, NH (US); Jonathan Kohanski, Nashua, NH (US); Bryan Hotaling, Harvard, MA (US)

(73) Assignee: Matrix Technologies LLC, Waltham, MA (US)

( * ) Notice: Subject to any disclaimer, the term of this patent is extended or adjusted under 35 U.S.C. 154(b) by 0 days.

(21) Appl. No.: 13/188,518

(22) Filed: Jul. 22, 2011

(65) Prior Publication Data

US 2012/0100047 A1 Apr. 26, 2012

Related U.S. Application Data

(60) Provisional application No. 61/367,216, filed on Jul. 23, 2010.

(51) Int. Cl.
*B01L 3/02* (2006.01)
*G01N 35/10* (2006.01)

(52) U.S. Cl.
CPC .............................. *G01N 35/1074* (2013.01)

(58) Field of Classification Search
CPC ......... B01L 3/02; B01L 3/0275; G01N 35/10; G01N 35/1002; G01N 2035/103; G01N 35/1074

(Continued)

(56) References Cited

U.S. PATENT DOCUMENTS 3,498,342 A 3/1970 Sanderson
3,650,306 A 3/1972 Lancaster
(Continued)

FOREIGN PATENT DOCUMENTS

CN 101180544 A 5/2008
EP 0475517 A2 3/1992
(Continued)

OTHER PUBLICATIONS

Tecan Group Ltd. "Tecan introduces: Freedom EVO, a new state-of-the art automation platform that evolves with the changing needs of today's laboratory," Tecan Group Ltd—Customer News (Jul. 2, 2003) available at <http://www.tecan.com/page/content/printasp?print=yes&Id=3800&MenuID=2185&ConID=3800>, accessed on Aug. 10, 2011.

(Continued)

*Primary Examiner* — Brian R Gordon
(74) *Attorney, Agent, or Firm* — Wood Herron & Evans LLP

(57) ABSTRACT

A liquid handling system that is configured to receive an interchangeable pipetting head that is selected from a plurality of interchangeable pipetting heads for automated liquid handling flexibility and scalability. The system includes a housing and at least one pipetting head disposed within that housing for aspirating and dispensing a liquid. A locking mechanism interchangeably receives the at least one pipetting head and includes an adaptor plate and a support block. The adaptor plate is operably coupled to the housing and the support block is operably coupled to the at least one pipetting head. The support block is then, in turn, is configured to be operably coupled to the adaptor plate.

21 Claims, 30 Drawing Sheets

(58) Field of Classification Search
USPC .............. 422/501, 504–505, 509, 511, 521, 422/524–525, 564
See application file for complete search history.

(56) References Cited

U.S. PATENT DOCUMENTS

| | | | |
|---|---|---|---|
| 4,106,911 A | 8/1978 | Marcelli | |
| 5,111,703 A | 5/1992 | Allen | |
| 5,139,744 A | 8/1992 | Kowalski | |
| 5,232,664 A * | 8/1993 | Krawzak | G01N 35/1002 422/523 |
| 5,525,302 A | 6/1996 | Astle | |
| 5,627,522 A | 5/1997 | Walker et al. | |
| 5,958,343 A | 9/1999 | Astle | |
| 6,182,719 B1 | 2/2001 | Yahiro | |
| 6,589,483 B1 * | 7/2003 | Maeda | 422/525 |
| 6,982,063 B2 | 1/2006 | Hamel et al. | |
| 7,284,454 B2 | 10/2007 | Cote | |
| 7,291,309 B2 * | 11/2007 | Watson et al. | 422/63 |
| 7,314,598 B2 * | 1/2008 | Nishino | 422/501 |
| 7,416,709 B1 | 8/2008 | Martin et al. | |
| 7,416,710 B1 | 8/2008 | Martin et al. | |
| 7,431,768 B1 | 10/2008 | Martin et al. | |
| 7,431,769 B1 | 10/2008 | Martin et al. | |
| 7,435,379 B1 | 10/2008 | Martin et al. | |
| 7,435,397 B1 | 10/2008 | Martin et al. | |
| 7,452,419 B1 | 11/2008 | Martin et al. | |
| 7,462,327 B2 | 12/2008 | Meinicke et al. | |
| 7,510,690 B1 | 3/2009 | Martin et al. | |
| 7,585,463 B2 * | 9/2009 | Austin et al. | 422/63 |
| 7,713,481 B2 | 5/2010 | Naumann | |
| 7,858,041 B2 * | 12/2010 | Muraishi et al. | 422/511 |
| 7,897,111 B2 * | 3/2011 | Naumann | 422/511 |
| 2001/0019845 A1 * | 9/2001 | Bienert et al. | 436/181 |
| 2002/0051737 A1 * | 5/2002 | Sollbohmer | G01N 35/1065 422/400 |
| 2002/0176803 A1 | 11/2002 | Hamel et al. | |
| 2003/0027345 A1 | 2/2003 | Friswell et al. | |
| 2003/0215360 A1 * | 11/2003 | Ruddock | 422/63 |
| 2004/0071602 A1 * | 4/2004 | Yiu | 422/100 |
| 2007/0053797 A1 * | 3/2007 | Muraishi et al. | 422/100 |
| 2007/0059206 A1 * | 3/2007 | Araki et al. | 422/65 |
| 2009/0129985 A1 * | 5/2009 | Ikushima | 422/100 |
| 2011/0268627 A1 * | 11/2011 | Warhurst et al. | 422/511 |
| 2011/0268628 A1 * | 11/2011 | Warhurst et al. | 422/511 |
| 2014/0004020 A1 * | 1/2014 | Tubbs et al. | 422/509 |

FOREIGN PATENT DOCUMENTS

| | | |
|---|---|---|
| EP | 1884781 A1 | 2/2008 |
| FR | 2525770 A1 | 10/1983 |
| FR | 2597607 A1 | 10/1987 |
| JP | 11326341 A | 11/1999 |
| JP | 2004528977 A | 9/2004 |
| JP | 2007139719 A | 6/2007 |
| WO | 02096562 A1 | 12/2002 |
| WO | 2006123690 A1 | 11/2006 |

OTHER PUBLICATIONS

Beckman Coulter, Inc. "Flexible solutions for confidence in results. BIOMEK FXP laboratory automation workstation," Product Brochure No. BR-10149B (2006) available at <https://www.beckmancoulter.com/wsrportal/bibliography?docname=BR-10149B.pdf>, accessed on Aug. 10, 2011.
Beckman Coulter, Inc. "Flexible solutions for confidence in results. BIOMEK NXP laboratory automation workstation," Product Brochure No. BR-101450B (2006) available at <https://www.beckmancoulter.com/wsrportal/bibliography?docname=BR-10150B.pdf>, accessed on Aug. 10, 2011.
Hamilton Bonaduz AG, "Microlab Star Line" Product Brochure No. BR-0502-10/01 (Aug. 2004) available at <http://www.hamiltonrobotics.com/fileadmin/user_upload/products/startour/MR-0805-03_STAR_LINE_web.pdf>, accessed on Aug. 10, 2011.
Hamilton Storage Technologies, Inc. "Microlab Nimbus automated pipetting platform," News (Feb. 2008) available at <http://www.hamiltonrobotics.com/print/top-menu/news/news/details/browse/1/news/microlabR-n/?tx_ttnews%5BbackPid%5D=71&cHash=1d36aefb24>, accessed on Oct. 17, 2011.
Agilent Technologies. "Agilent Vertical Pipetting Station," Product Brochure No. 5990-3481EN (2009) available at <http://www.chem.agilent.com/Library/datasheets/Public/5990-3481EN_LO.pdf>, accessed on Aug. 10, 2011.
Thermo Fisher Scientific. "Thermo Scientific Matrix PlateMate Plus," Product Brochure No. P-2007-0056_RevB (2007) available at <http://www.matrixtechcorp.com/downloads/P-2007-0056_ALHSPSPMP_RevB.pdf>, accessed on Aug. 10, 2011.
Eppendorf AG. "I love high performance: automated pipetting systems with integrated Thermomixer," Product Brochure No. A507 X13 (2009) available at <http://www.eppendorf.com/int/index.php?sitemap=2.3&pb=592447b1db3faedd&action=products&contentid=1&catalognode=69733&productpage=1>, accessed on Aug. 10, 2011.
Thermo Fisher Scientific. "Thermo Scientific Matrix Hydra II," Product Brochure No. P-2007-0202 (2008) available at <http://www.matrixtechcorp.com/downloads/Hydra_II_Spec_Sheet_FINAL.pdf>, accessed on Aug. 10, 2011.
Thermo Fisher Scientific. "Thermo Scientific Matrix Hydra DT," Product Brochure No. P-2007-0161 (2007) available at <http://www.matrixtechcorp.com/downloads/HydraDTSpecSheet_FINAL.pdf>, accessed on Aug. 10, 2011.
Apricot Designs. "i-Pipette Series," Product Brochure (2010) available at <http://www.apricotdesigns.com/downloads/ApricotDesigns_i-pipetteSeries.pdf>, accessed on Aug. 10, 2011.
Cybio AG. "SELMA," Product Brochure No. 06.14.01.01 (2010) available at <http://www.lab-services.nl/labservices/media/cybio/CyBio_SELMA_English.pdf>, accessed on Aug. 10, 2011.
Rainin Instrument, LLC. "Rainin: Liquidator 96 ready-to-use manual benchtop system," Nature Methods (Jun. 2008) pp. iii-iv, available at <http://www.nature.com/nmeth/journal/v5/n6/pdf/nmeth.f.214.pdf>, accessed on Aug. 10, 2011.
Caliper Life Sciences, Inc., "Zephyr: Compact Liquid Handler," Product Brochure No. ZH-BR-01 (Nov. 2009) available at <http://www.caliperls.com/assets/024/8560.pdf>, accessed on Aug. 10, 2011.
Caliper Life Sciences, Inc., "RapidPlate 96/384 Workstation," Product Brochure No. RP3 03/04 (2004) available at <http://www.ietltd.com/pdf_datasheets/RapidPlate%20Data%20Sheet.pdf>, accessed on Aug. 10, 2011.
PerkinElmer Life and Analytical Sceincies. "JANUS automated workstation," Product Brochure 007649_01 (2007) available at <http://www.perkinelmer.com/CMSResources/Images/44-73222BRO_JANUS_overview.pdf>, accessed on Aug. 10, 2011.
Espacenet, EPO Machine Translation of Application No. FR2525770 (A1), Published Oct. 28, 1983, http://worldwide.espacenet.com/publicationDetails/biblio?DB=worldwide.espacenet.com&II=0&ND=3&adjacent=true&locale=en_EP&FT=D&date=19831028&CC=FR&NR=2525770A1&KC=A1, retrieved on Mar. 6, 2012 (5 pages).
Espacenet, EPO Machine Translation of Application No. FR2597607 (A1), Published Oct. 23, 1987, http://worldwide.espacenet.com/publicationDetails/biblio?DB=worldwide.espacenet.com&II=0&ND=3&adjacent=true&locale=en_EP&FT=D&date=19871023&CC=FR&NR=2597607A1&KC=A1, retrieved on Mar. 6, 2012 (9 pages).
U.S. Patent and Trademark Office, International Search Report and Written Opinion in corresponding PCT Application No. PCT/US2011/045163 mailed Dec. 12, 2011, 10 pages.
Espacenet, English Machine Translation of CN101180544A, published May 14, 2008, retrieved from http://worldwide.espacenet.com on Jul. 1, 2015 (13 pages).
Chinese Patent Office, Second Office Action, Application No. 201180044450.5, mailed Jun. 19, 2015 (7 pages).

(56) References Cited

OTHER PUBLICATIONS

Chinese Patent Office, English Translation of Second Office Action, Application No. 201180044450.5, mailed Jun. 19, 2015 (5 pages).
Canadian Intellectual Property Office, Second Office Action, Application No. 2,806,425, mailed Jul. 7, 2015 (4 pages).
Australian Government, Patent Examination Report No. 1, Patent Application No. 2011280928, date of issue Aug. 7, 2013 (4 pages).
Japanese Patent Office, Office Action, Japanese Patent Application No. 2013-520900, mailed Apr. 27, 2015 (4 pages).
Japanese Patent Office, English Translation of Office Action, Japanese Patent Application No. 2013-520900, mailed Apr. 27, 2015 (5 pages).
Japanese Patent Office, English Patent Abstract of JP2007139719A, published Jun. 7, 2007 (1 page).
Chinese Patent Office, Fourth Office Action and Search Report, Application No. 201180044450.5, dated Nov. 15, 2016 (11 pages).

* cited by examiner

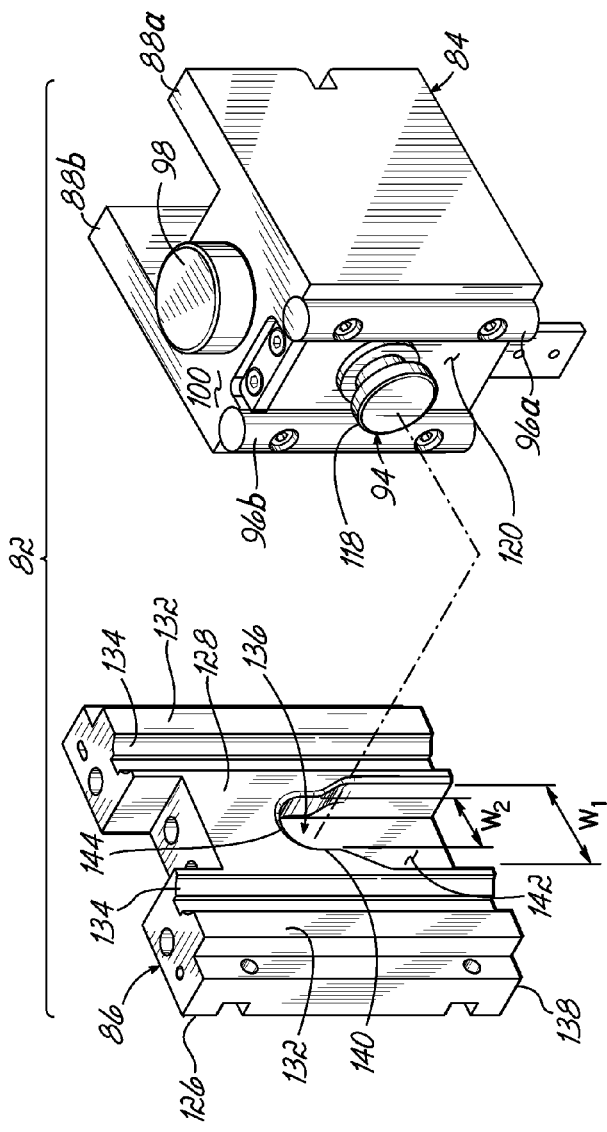
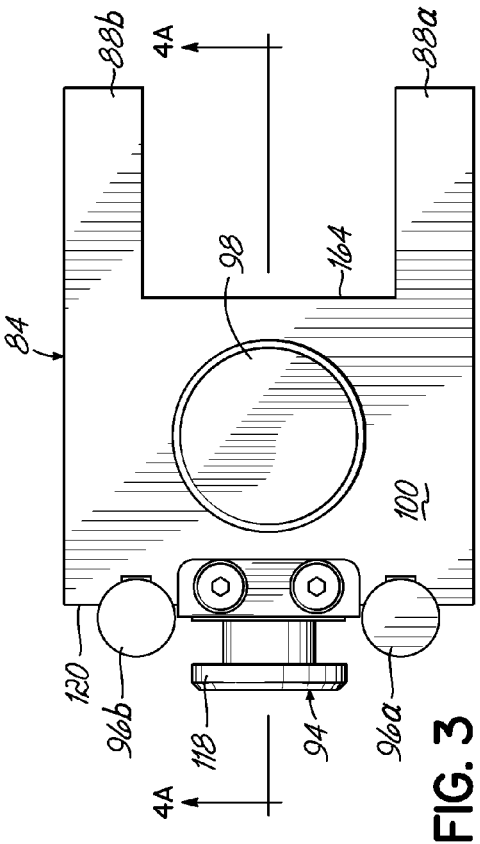
FIG. 2
FIG. 3

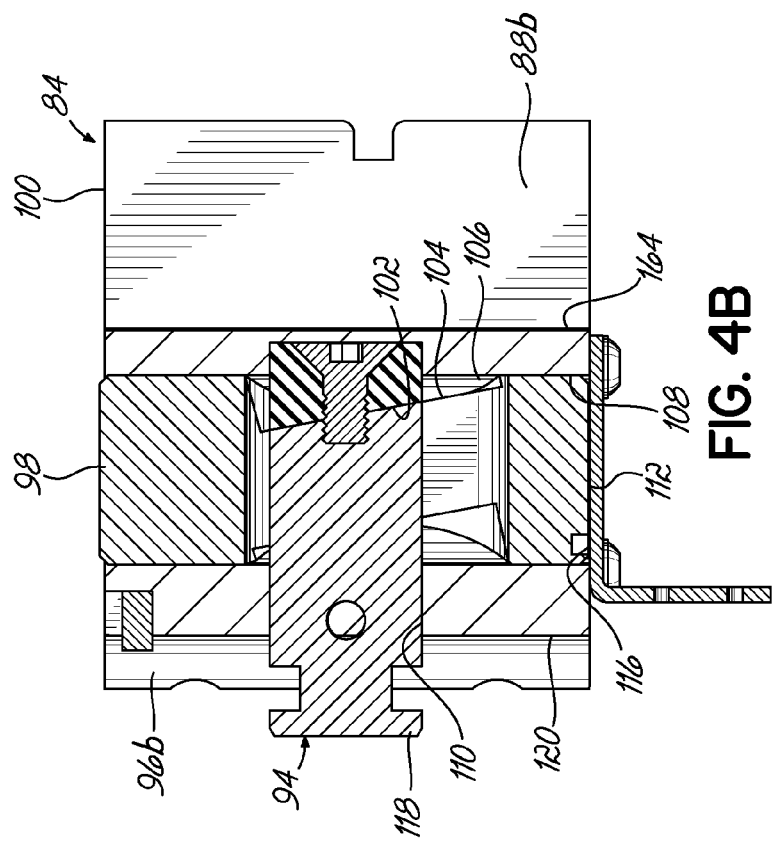
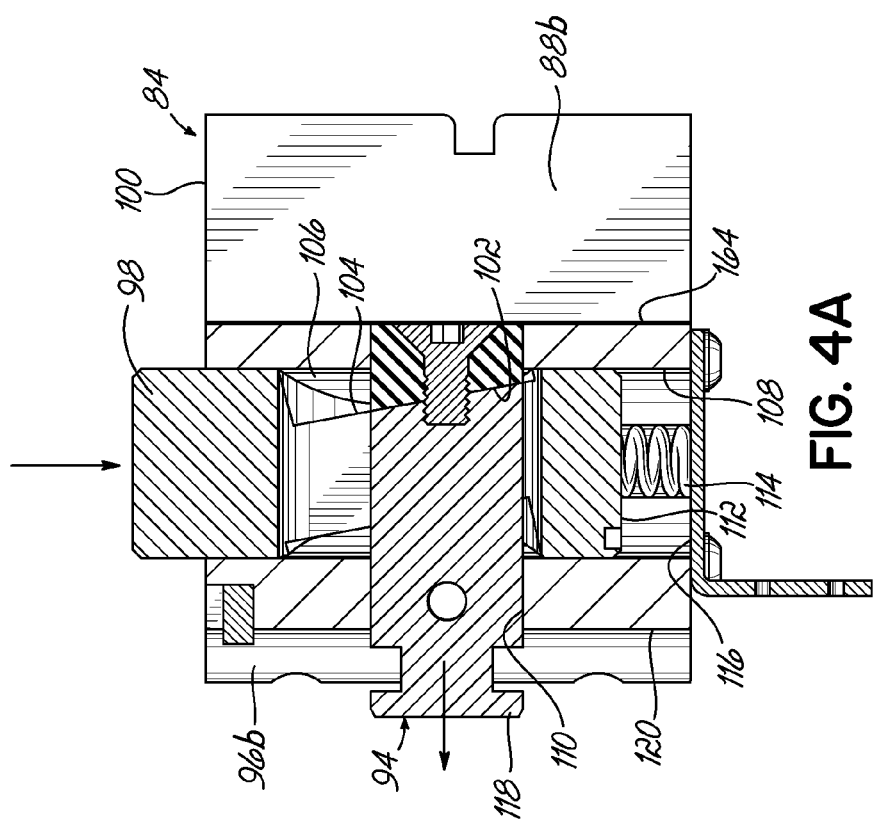

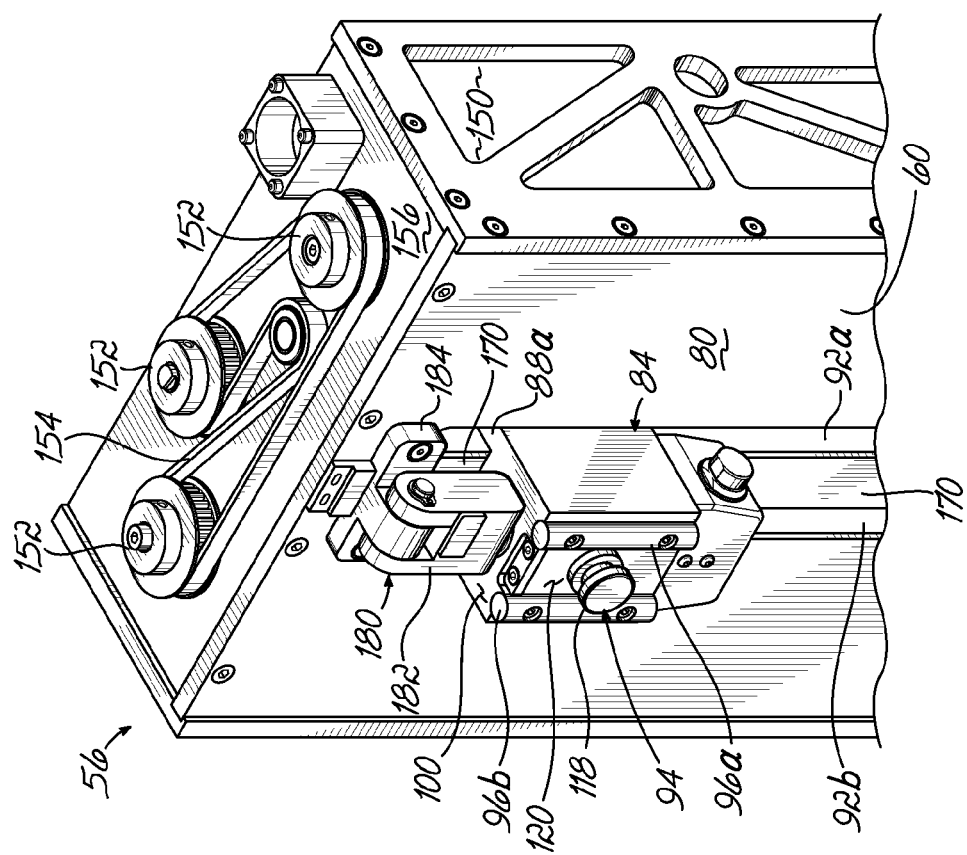

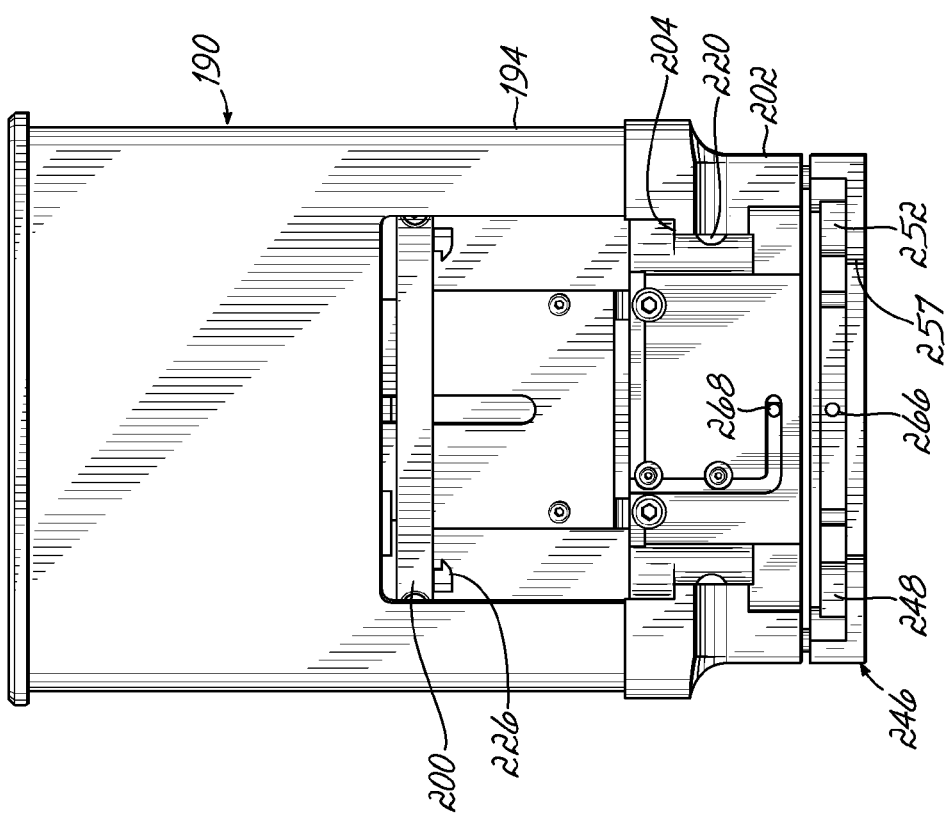

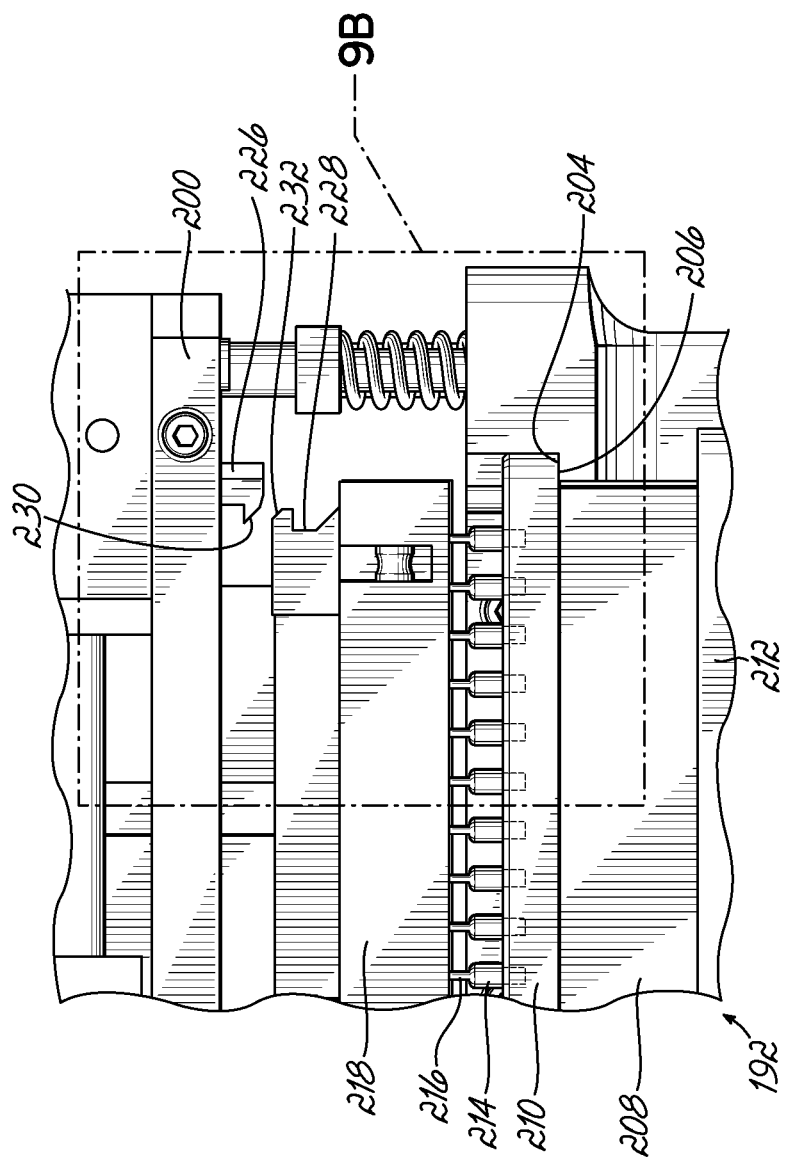

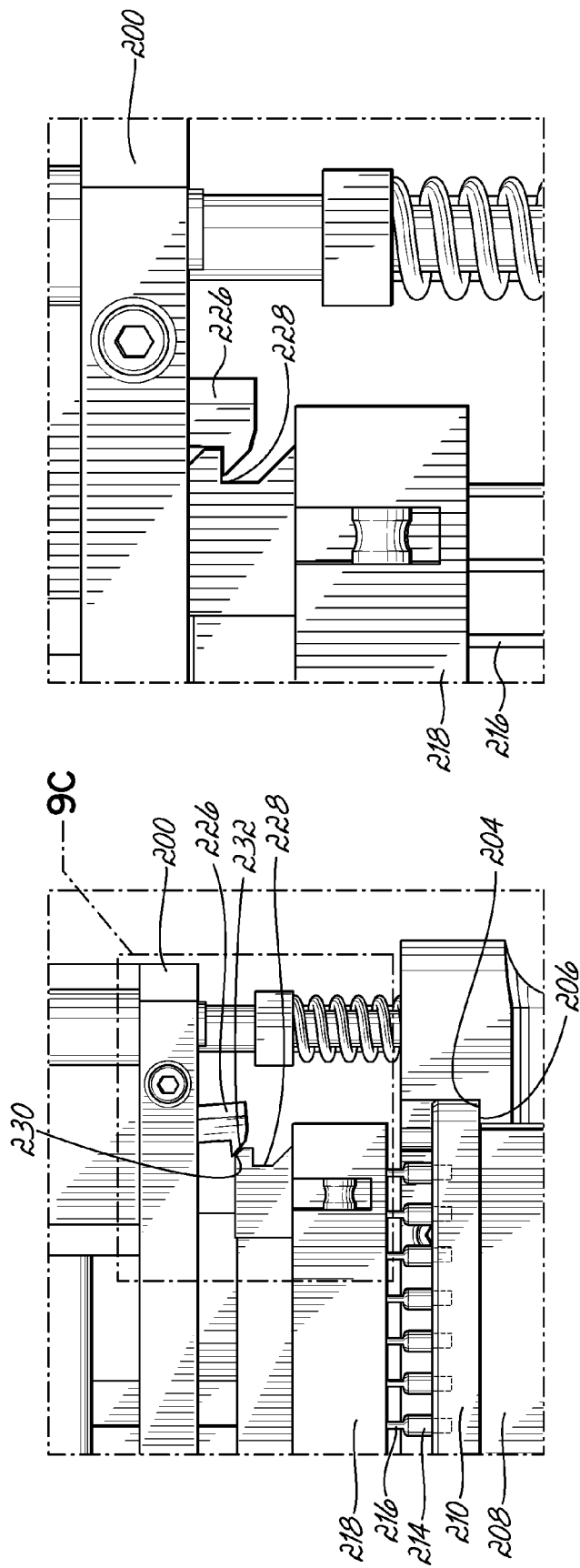

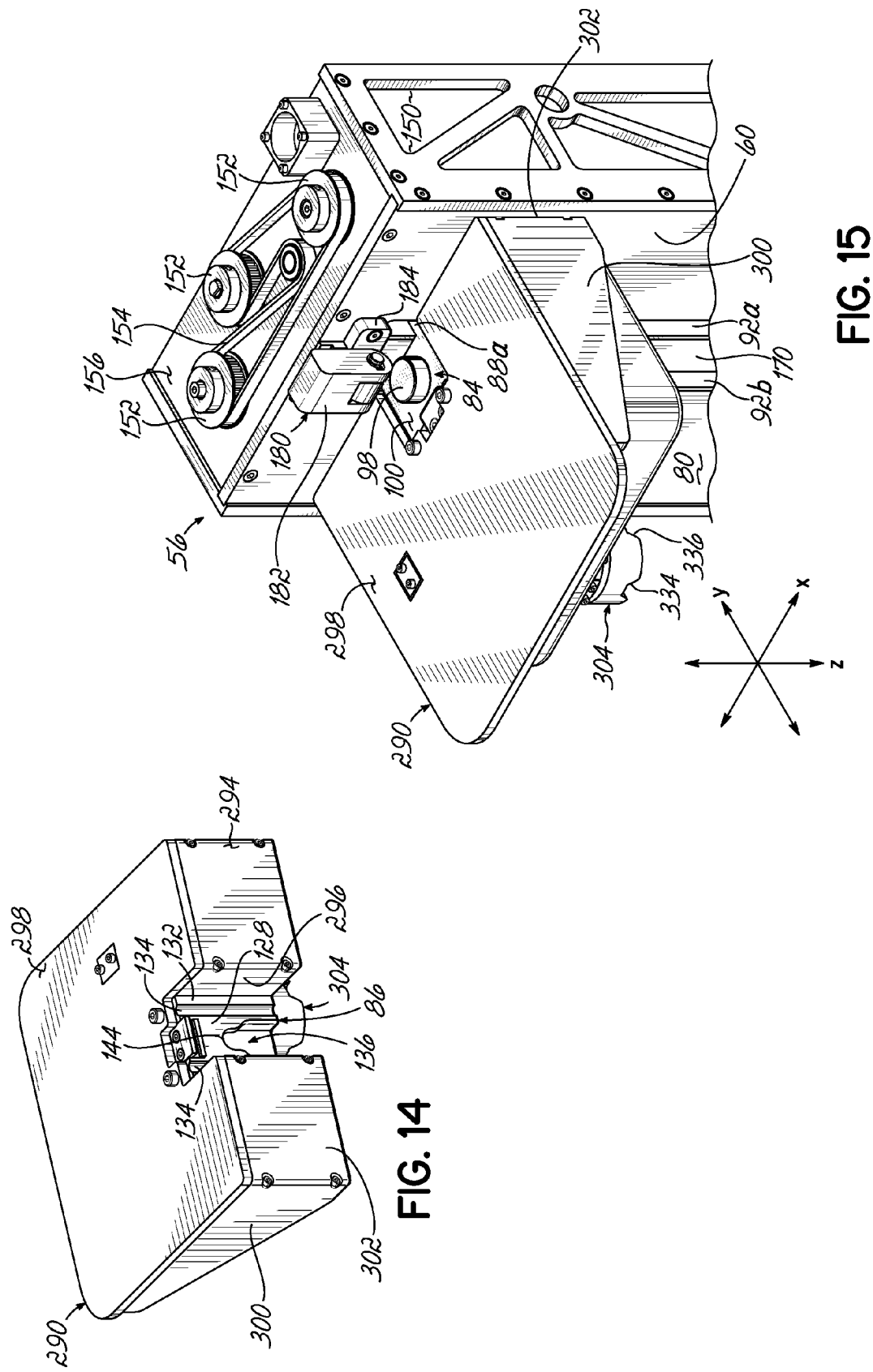

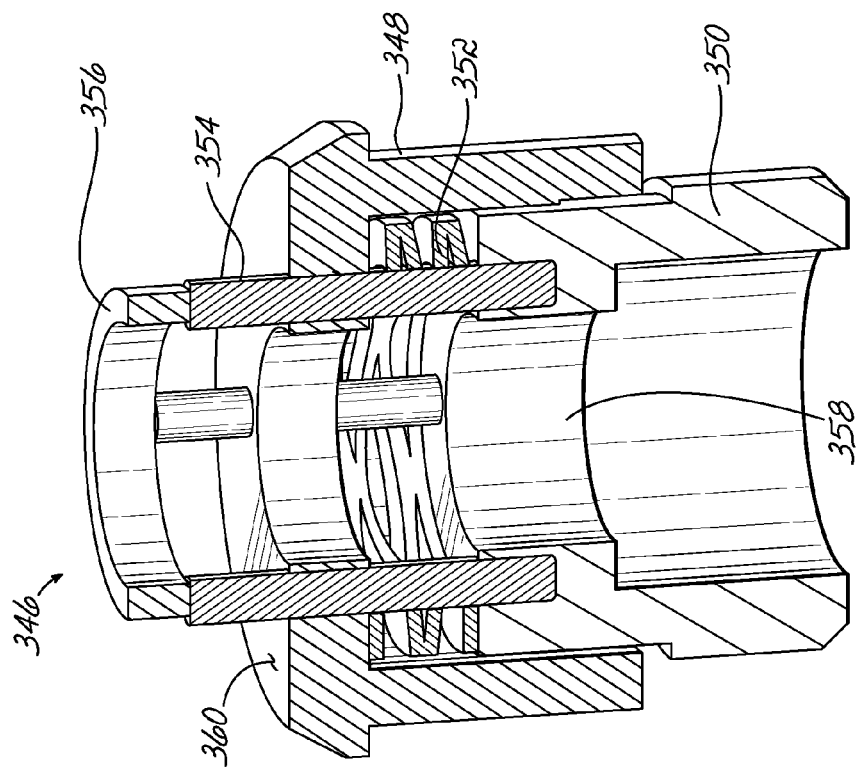
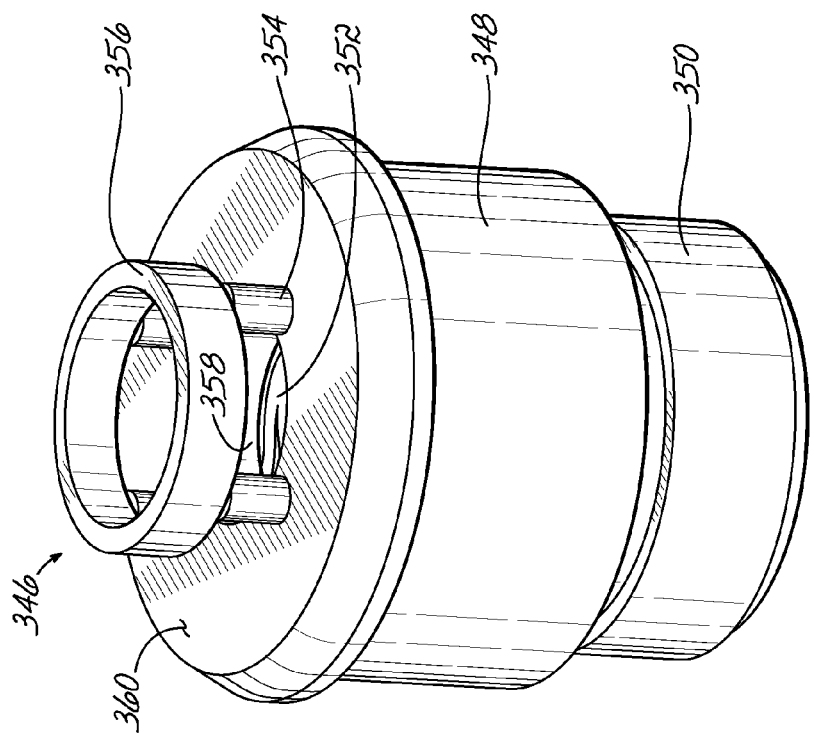

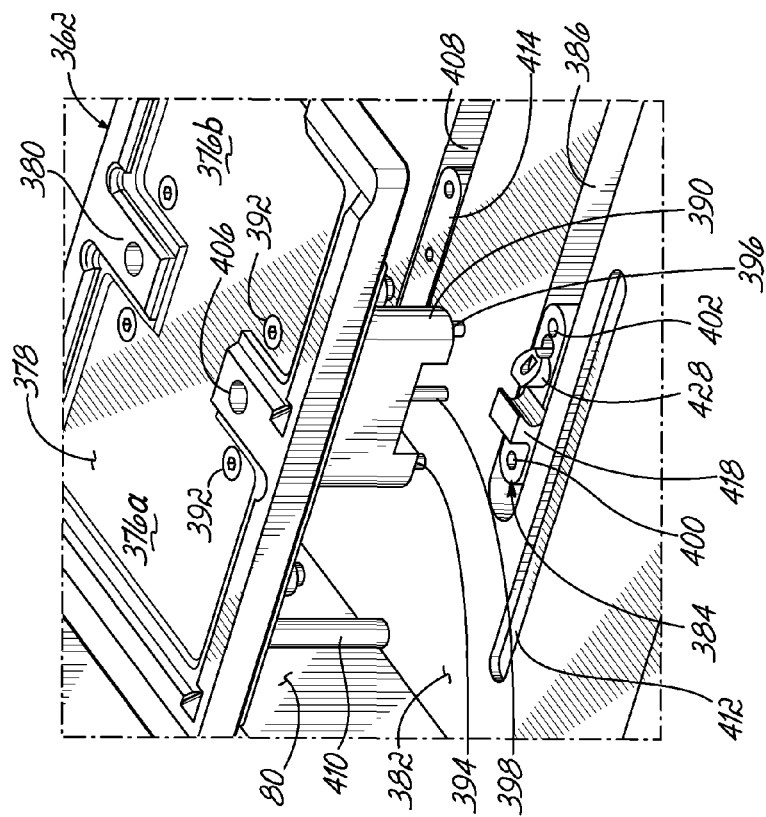
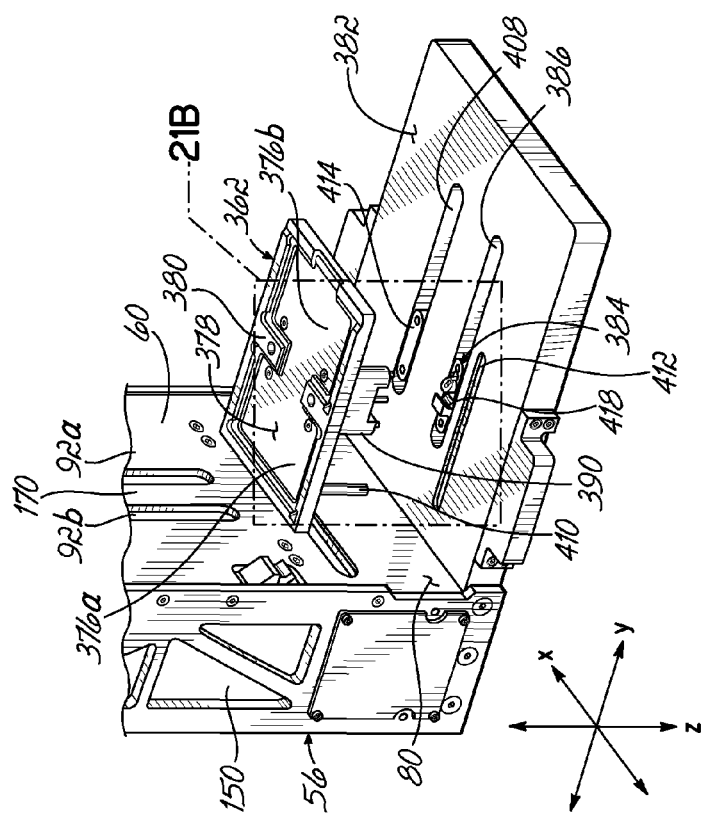
FIG. 21B
FIG. 21A

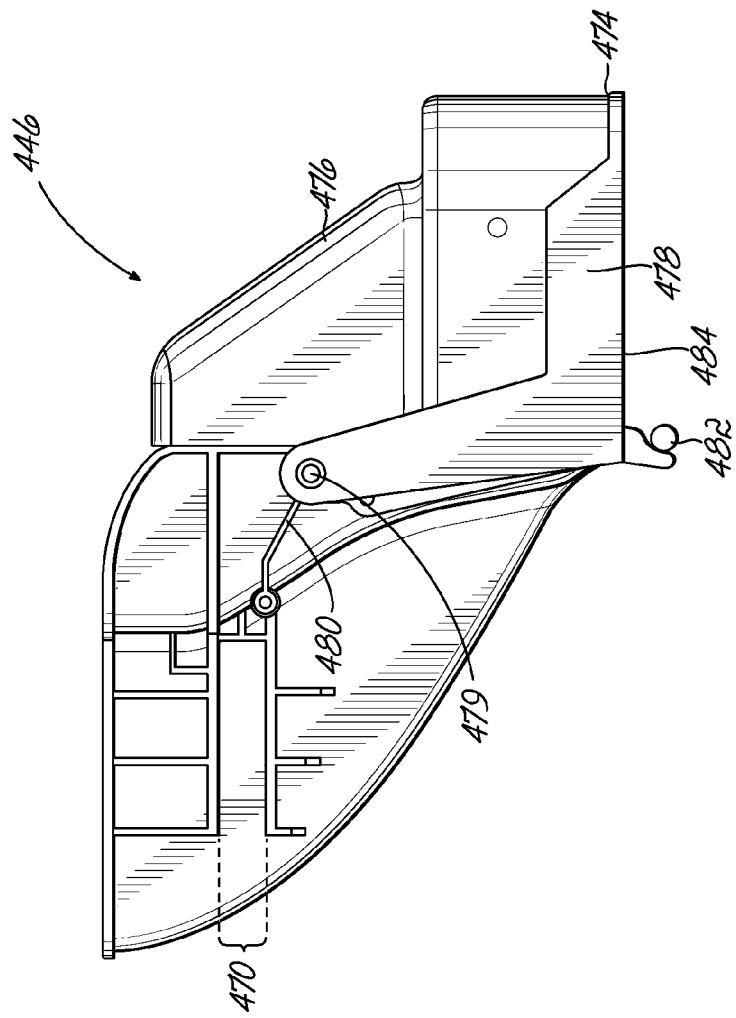
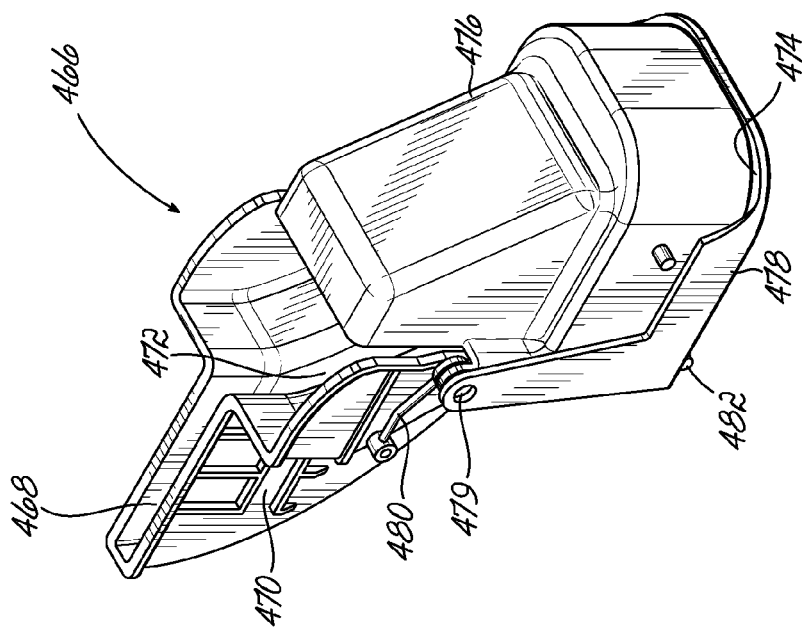
FIG. 27B
FIG. 27A

AUTOMATED LIQUID HANDLING DEVICE

The present application claims the filing benefit of co-pending U.S. Provisional Patent Application No. 61/367,216, filed on 23 Jul. 2010, the disclosure of which is hereby incorporated by reference herein in its entirety.

FIELD OF THE INVENTION

The present invention relates generally to automated liquid handling systems and, more particularly, to an automated pipetting system for use in laboratories and other environments.

BACKGROUND OF THE INVENTION

Sample preparation has conventionally been accomplished either by hand or by expensive, highly specialized automated systems that are limited in functionality. For example, the conventional automated systems are generally limited in their pipetting capacities and/or may require a particular type, brand, arrangement, or volume capacity labware. Therefore, each biomolecular technique or assay may require a separate automated system for achieving high-throughput analysis and data. For those laboratories of limited resources, individualized systems are not economically feasible and the laboratory may be limited to sample preparation by hand, which results in decreased throughput and potentially increased pipetting variation and error.

There remains a need for a fully automated sample preparation system that adaptable to a wide range of techniques. Further, the sample preparation system would preferably interface with other sample handling systems and to grow with the increasing needs of the laboratory.

SUMMARY OF THE INVENTION

The present invention overcomes the foregoing problems and other shortcomings, drawbacks, and challenges of conventional liquid handling systems by increasing liquid handling flexibility and automating liquid handling scalability. While the present invention will be described in connection with certain embodiments, it will be understood that the present invention is not limited to these embodiments. To the contrary, this invention includes all alternatives, modifications, and equivalents as may be included within the spirit and scope of the present invention.

Various embodiments of the present invention, as described herein, are directed to an automated liquid handling system that offers a range of pipetting options. The automated liquid handling system may include interchangeable pipetting heads, each having a one or more fluid channels in a particular spatial arrangement and configured to aspirate and dispense a particular volume of liquid for carrying out a biomolecular technique or assay in a high throughput or batch-mode manner.

According to one embodiment of the present invention, a liquid handling system is provided that is configured to receive a pipetting head that is selected from a plurality of interchangeable pipetting heads. The system includes a housing and at least one pipetting head disposed within that housing for aspirating and dispensing a liquid. A locking mechanism interchangeably receives the at least one pipetting head and includes an adaptor plate and a support block. The adaptor plate is operably coupled to the housing and the support block is operably coupled to the at least one pipetting head. The support block is further configured to be operably coupled to the adaptor plate.

According to another embodiment of the present invention, a pipetting head locking mechanism is provided. The locking mechanism includes an adaptor that is operably coupled to the liquid handling system and a support block that is operably coupled to the pipetting head. The support block has a housing with a plunger and a locking pin disposed therein. Both of the plunger and the locking pin are moveable relative to the housing. Movement of the plunger moves the locking pin from a retracted position to an extended position, wherein when the locking pin is in the extended position, the support block may be received by or removed from the adaptor plate.

In accordance with another embodiment of the present invention, a pump actuating mechanism for a matrix-style pipetting head is provided. The matrix-style pipetting head is received by a housing having a motor operably coupled thereto. The motor, which is operably coupled to the housing, actuates a dispenser mechanism within the matrix-style pipetting head. A plunger plate within the housing interfaces the motor with the matrix-style pipetting head.

Still another embodiment of the present invention is directed to a liquid handling device for an array-style pipetting head. The device includes an alignment block that receives the array-style pipetting head. A motor, which is operably coupled to the alignment block, actuates a dispenser mechanism within the array-style pipetting head.

Another embodiment of the present invention includes an adjustable stage, which is configurable to a desired number of workable surfaces. The adjustable stage includes a plurality of workable surface, each of which is configured to receive a labware. A first one of the workable surfaces is supported by a first moveable support; a second one of the workable surfaces is supported by a second moveable support. The second movable support moves between first and second positions. In the first position, the second one of the workable surfaces resides above the first one of the workable surfaces. In the second position, the second one of the workable surfaces is offset from the first one of the workable surfaces.

According to another embodiment of the present invention, a tip ejection apparatus is described for use with a liquid handling system. The tip ejection apparatus includes a tip receiving well that receives disposable pipetting tips from a pipetting head. An ejection port extends from the tip receiving well for collecting and releasing the disposable pipetting tips. A rotatable mouth is operably coupled to the ejection port. In a first position, the rotatable mouth retains the collected disposable pipetting tips in the ejection port. In a second position, the rotatable mouth releases the collected disposable pipetting tips from the ejection port.

The above and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the present invention and, together with a general description of the invention given above, and the detailed description of the embodiments given below, serve to explain the principles of the present invention.

FIG. 2 is a perspective view of one embodiment of a support block and an adaptor plate comprising a locking mechanism.

FIG. 3 is a top plan view of the support block shown in FIG. 2.

FIGS. 4A-4B are cross-sectional views of the support block taken along the line 4A-4A in FIG. 3.

FIGS. 5A-5C are perspective views of an upper housing of the automated liquid handling device of FIG. 1 illustrating vertical translation the support block of FIG. 2.

FIG. 7 is a front view of the cage without the matrix-style pipetting head.

FIGS. 9A-9C are enlarged front elevational views illustrating coupling of the matrix-style pipetting head with the cage.

FIG. 14 is a perspective of an adaptor cage for receiving and actuating a single or linear array pipetting head.

FIG. 15 is a perspective view of the adaptor cage of FIG. 14 mounted to the upper housing of the automated liquid handling device of FIG. 1.

FIGS. 18A and 19A are perspective views of a crash prevention device in a relaxed and an activated state, respectively.

FIGS. 18B and 19B are cross-sectional view through the crash prevention devices of FIGS. 18A and 19A, respectively.

FIGS. 21A and 22A are perspective views of a tray supporting surface positioned above and coupled to the bottom surface of the lower housing, respectively.

FIGS. 21B and 22B are enlarged perspective views of the tray supporting surface as shown in FIGS. 21A and 22A, respectively.

FIGS. 27A and 28A are perspective views of the tip ejection apparatus with the ejection port in the closed and opened positions, respectively.

FIGS. 27B and 28B are side elevational views of the tip ejection apparatus as shown in FIGS. 27A and 27B, respectively.

DETAILED DESCRIPTION

Figure 1:
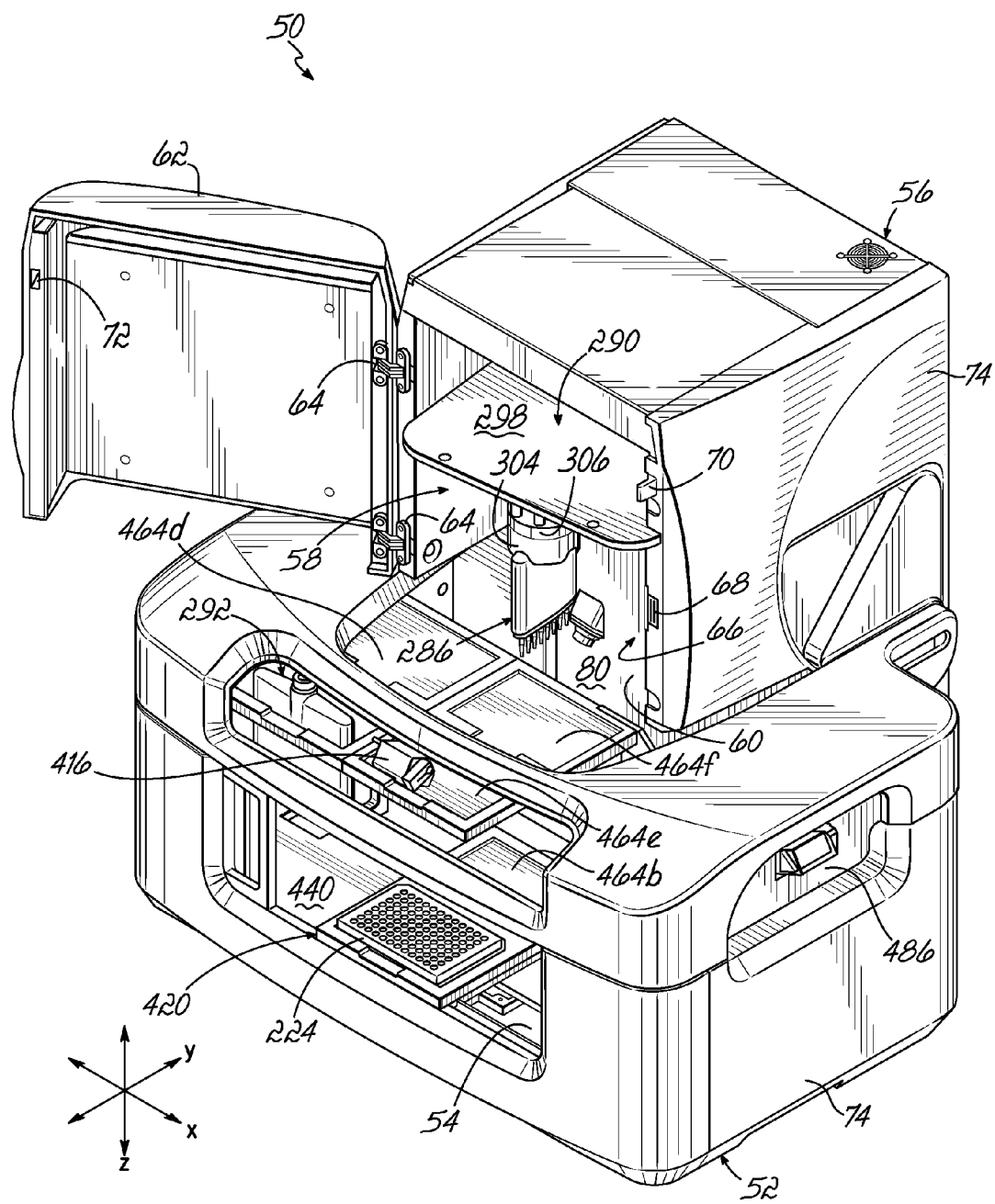
FIG. 1 is a perspective view of an automated liquid handling device according to one embodiment of the present invention.

Referring to the figures, and particularly to FIG. 1, an automated liquid handling device 50 according to one embodiment of the present invention includes a lower housing 52 (i.e., a first housing) for enclosing a workspace 54 and an upper housing 56 (i.e., a second housing) for enclosing a liquid handling system 58. It will be understood that the upper and lower housings 56, 52 may be formed as an integral housing, which may share a common rear wall 60 (FIG. 5A), or at least a portion of the rear wall 60 (FIG. 5A). The upper housing 56 may also include a door 62, coupled to the upper housing 56 by one or more hinges 64, for accessing an internal chamber 66 of the upper housing 56 and for changing liquid handling systems 58 and/or including a liquid handling system accessory as will be described in more detail below. The door 62 may further include a magnetic latch 68 and/or a hook latch 70 received by an opening 72 of the door to secure and/or lock the door 62 with a sidewall 74 of the upper housing 56.

The liquid handling system 58 within the upper housing 56 is adapted to vertically translate along an inner surface 80 of the rear wall 60. The upper housing 56 is adapted to allow for a rapid exchange between various types of liquid handling systems 58, various embodiments of which are described in detail below. Generally, the system 50 is configured such that various embodiments of the liquid handling system 58 may be mounted within the upper housing 56 via a locking mechanism 82, which is shown and described in FIGS. 2-4B.

In FIG. 2, the illustrative locking mechanism 82 includes a support block 84 and an adaptor plate 86. The support block 84 has at least one laterally displaced flange or arm (two arms 88a, 88b are shown) that extends rearwardly and is spaced to extend through an opening (two openings 92a, 92b (FIG. 5A) are shown corresponding to arms 88a, 88b, respectively) provided in the rear wall 60 of the upper housing 56. The support block 84 further includes a forwardly-extending locking pin 94 and laterally positioned bearing ribs 96a, 96b that project from the support block 84 in a direction that generally opposes the arms 88a, 88b.

A plunger 98 is positioned perpendicular to the locking pin 94 and extending upwardly from a top surface 100 of the support block 84. The locking pin 94 and the ribs 96a, 96b are operable for coupling the support block 84 to the adaptor plate 86 in a manner that is described below and in a manner to facilitate the rapid exchange of the liquid handling system 58.

Within the support block 84, the plunger 98 and the locking pin 94 engage at a pair of corresponding angled surfaces 102, 104. As shown in FIG. 4A, the first of the angled surfaces 102 is formed on an internal end of the locking pin 94 and the second, corresponding angled surface 104 is created by a wedge 106 that is located within, surrounding, or otherwise associated with the plunger 98. The plunger 98 and the wedge 106 are located within a first bore 108 within the support block 84; the locking pin 94 is located within a second bore 110 that intersects (optionally, orthogonal to) the first bore 108.

The plunger 98 may be "T"-shaped so as to capture two plunger springs (only one spring 114) is shown between the top arms (not shown) of the plunger 98 and an internal bottom 116 of the support block 84. The plunger springs 114 bias the plunger 98 upwardly, as shown in FIG. 4A.

Referring now to both FIGS. 4A and 4B, operation of the plunger 98 and locking pin 94 are shown with greater detail. When a downwardly-directed force is applied to the plunger 98 of FIG. 4A, the plunger 98 is translated into and along the first bore 108 of the support block 84, against the bias of the spring 114. As the plunger 98 moves downward until the bottom surface 112 of the plunger 98 contacts the bottom surface 112 and the wedge 106 moves in a like manner. Continued downwardly-directed force applied to the plunger 98 moves the wedge 106 downward to the position shown in FIG. 4B. Downward movement of the wedge 106 translates the vertical motion of the plunger 98 to a horizontally-directed movement of the locking pin 94 within the second bore 110 via the corresponding angled surfaces 102, 104. In this way, downwardly-directed force applied to the plunger 98 displaces a head 118 on the locking pin 94 away from an outer side surface 120 of the support block 84.

With the head 118 of the locking pin 94 laterally extended from the outer side surface 120 in FIG. 4B, the support block 84 is poised to be received by the adaptor plate 86. Referring again to FIG. 2, the adaptor plate 86 may include a mounting surface 126 configured to be coupled to the liquid handling system 58 (FIG. 1) by a suitable securement device, for example, bolt, screw, or bonding agent. A locking side 128 opposes the mounting surface 126 and may include rails 132 and/or grooves 134 that are spaced and sized to slidably receive the ribs 96a, 96b of the support block 84. A keyed slot 136 extends upwardly from a bottom surface 138 of the adaptor plate 86 and converges from a wider first width, $w_1$, near the bottom surface 138 to a portion 140 having a narrower second width, $w_2$, that is spaced away from an inner, rear surface 142 of the adaptor plate 86 and that ultimately terminates at a closed end 144 positioned approximate centrally, or near the middle of, the adaptor plate 86.

In use, and with the locking pin 94 of the support block 84 extended laterally (as was shown in FIG. 4B), the head 118 of the locking pin 94 may slide upwardly from the bottom surface 138 of the adaptor plate 86 and enter the keyed slot 136. With continued upwardly-directed sliding of the support block 84, the head 118 slides between the narrowed-width portion 140 and the inner rear surface 142 of the adaptor plate 86.

With the support block 84 fully inserted into the keyed slot 136, the downwardly-directed force applied to the plunger 98 may be released. Release of the plunger 98 also releases the compression force applied to the plunger spring 114, causing the plunger spring 114 to relax and bias the plunger 98 upwardly. The wedge 106 associated with the plunger 98, moves upwardly with relaxation of the plunger spring 114 such that the corresponding angled surfaces 102, 104 translate the vertically-directed movement of the plunger 98 to a horizontally, and inwardly-directed movement of the locking pin 94. More specifically, the upwardly-directed movement of the plunger 98 and the wedge 106 translates to an inwardly-directed movement of the locking pin 94 to the position shown in FIG. 4A, which captures the narrowed-width portion 140 of the adaptor plate 86 between the head 118 of the locking pin 94 and the outer side surface 120 of the support block 84.

Figure 5B:
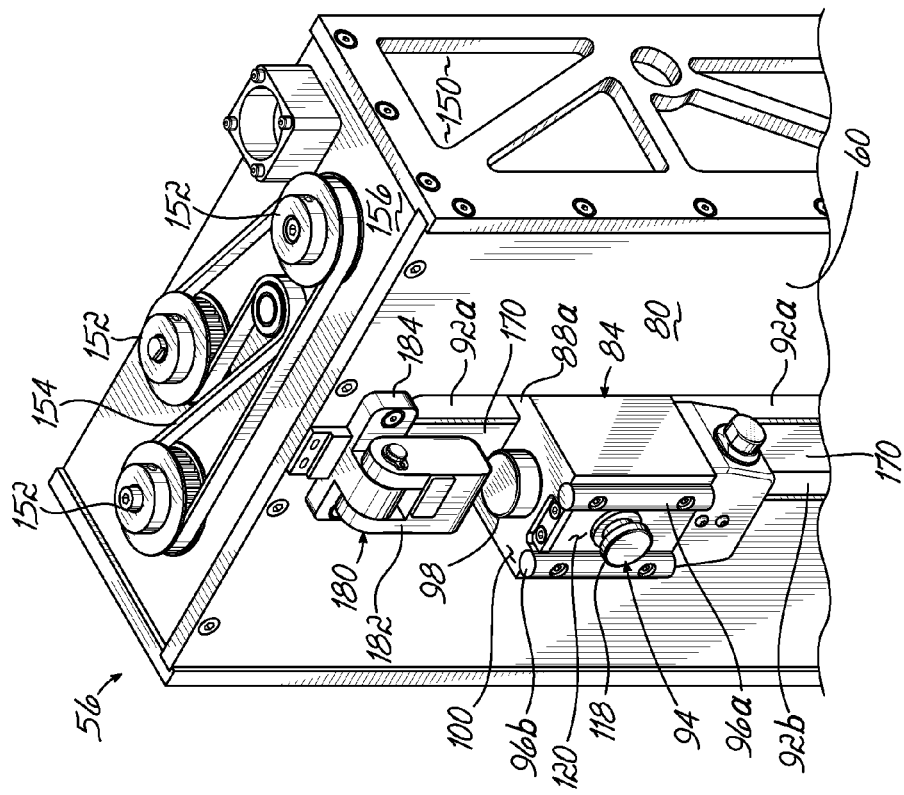
Figure 5A:
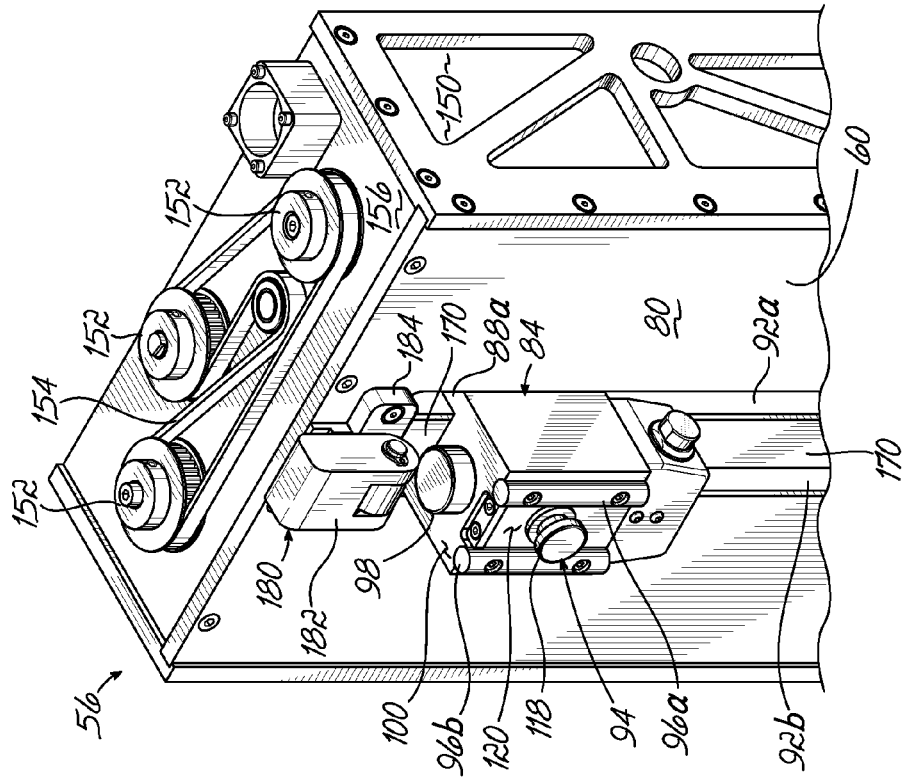

Referring now to FIGS. 5A-5C, vertical translation of the locking mechanism 82 within the automated liquid handling system 50 (FIG. 1) is described in accordance with one embodiment of the present invention. The locking mechanism 82 (only the support block 84 is shown in FIGS. 5A-5C) may be vertically translated along the rear wall 60 of the upper housing 56. For vertical translation, a motor (not shown) may be included in a motor chamber 150 located within the upper housing 56 and on the reverse side of the rear wall 60. As shown, a series of pulleys 152 and a belt 154 driven by the pulleys 152, are operably coupled to the motor (not shown) and positioned on a top surface 156 of the motor chamber 150. The motor (not shown) drives the pulleys 152 and the belt 154, in a known manner, to vertically translate the support block 84 of the locking mechanism 82 (FIG. 2) along the pair of openings 92a, 92b. One such motor and pulley assembly for liquid handling devices is described in greater detail in U.S. Pat. No. 6,982,063 by Hamel et al., entitled AUTOMATED PIPETTING SYSTEM, the disclosure of which is hereby incorporated herein by reference in its entirety. More specifically, although not shown, the motor may be operably coupled to at least one of the pulleys 152 by a shaft (not shown). Rotation of the shaft (not shown) and the associated pulley (152) is translated to rotation of the remaining pulleys (152) via the belt 154. The arms 88a, 88b (FIG. 2) of the support block 84 extending through the openings 92a, 92b within the rear wall 60 are adjoined across a divider 170 and operably coupled to the pulleys 152. As a result, a recessed surface 164 (FIG. 2) of the support block 84 slides along the divider 170.

A release member 180 is mounted on the divider 170, between the openings 92a, 92b and near the top surface 156 of the motor chamber 150. The release member 180 includes a release bar 182 hingedly-coupled to the rear wall 60 by a mount 184 so that the release bar 182 may rotate between an upwardly-directed position (FIG. 5A) to a downwardly-directed position (FIG. 5B). In FIG. 5A, while the release bar 182 is rotated to the upwardly-directed position, the plunger 98 of the support block 84 is fully extended and the head 118 of the locking pin 94 is in the resting position adjacent the outer side surface 120 and would lockingly engage the adaptor plate 86 (FIG. 2) if it were present.

In FIG. 5B, the user has rotated the release bar 182 to the downwardly-directed position. As the motor (not shown) is activated to direct the support block 84, the plunger 98 contacts or abuts the release bar 182. With continued upward movement of the support block 84 and as shown in FIG. 5C, the release bar 182 depresses the plunger 98, in a manner that is similar to the description with reference to FIG. 4B, which outwardly displaces the head 118 of the locking pin 94 away from the outer side surface 120 of the support block 84. Resultantly, the adaptor plate 86 (FIG. 2) would be removable from the support block 84.

With one method of vertical translation within the automated liquid handling device 50 described, a first embodiment of a liquid handling system 58 and use of the same are described with reference to FIGS. 6-13.

Figure 6:
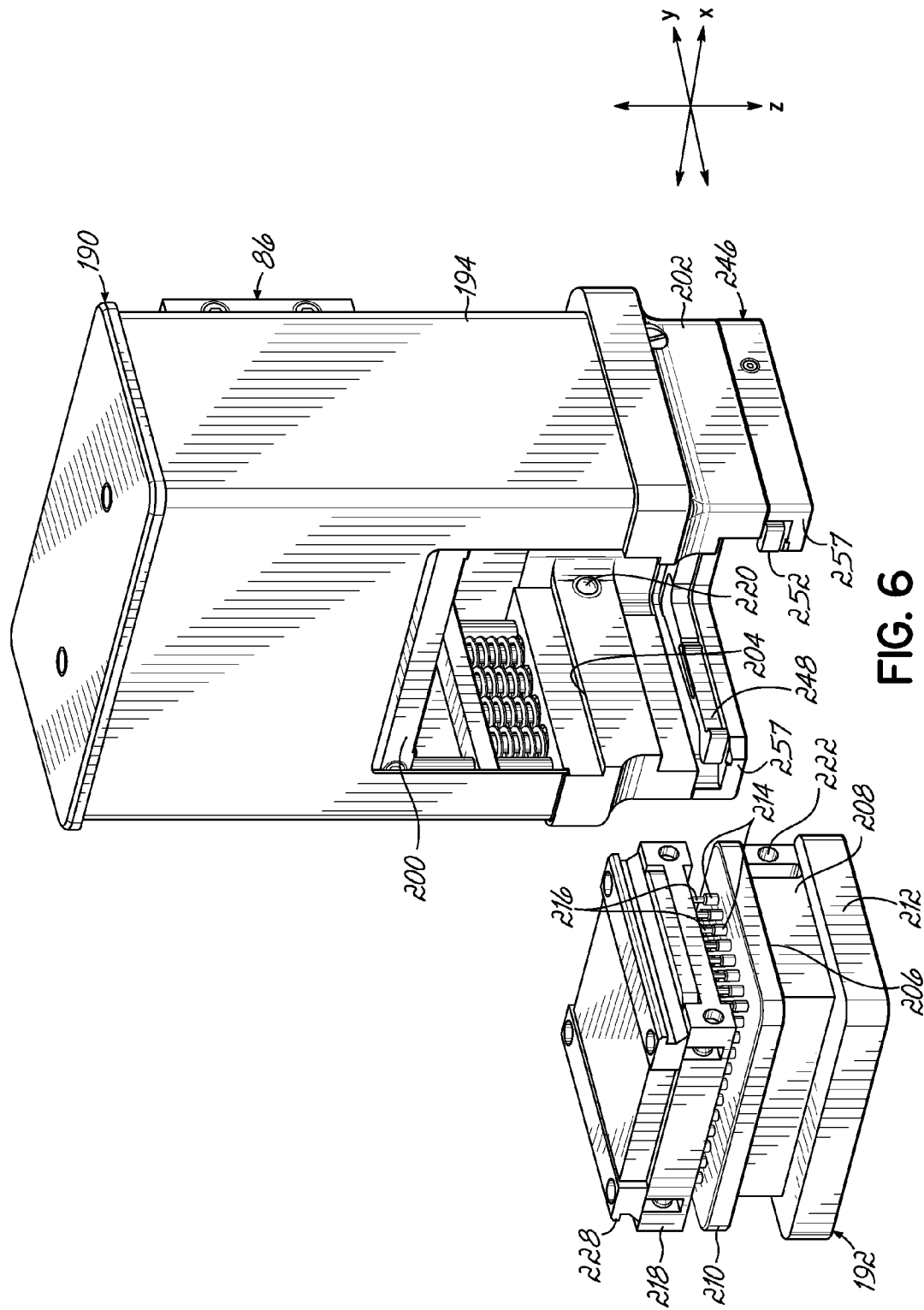
FIG. 6 is a perspective view of a cage for receiving and actuating a matrix-style pipetting head.

In FIG. 6, a cage 190 configured to engage and operate a matrix-style pipetting head 192 is shown. The cage 190 includes the adaptor plate 86 mounted on the back surface for rapidly coupling to and removal from the rear wall 60 (FIG. 5A) of the upper housing 56 (FIG. 1) via the locking mechanism 82 (FIG. 2).

The cage 190 is an electromechanical pump actuating mechanism for the matrix-style pipetting head 192 and includes a housing 194 enclosing a motor (not shown) and pulley system (not shown) for moving an actuating plate 200 vertically within the housing 194. The motor and pulley system (not shown) may be configured to operate in a manner that is consistent with the motor (not shown) and the pulley system 152 (FIG. 5A) associated with the upper housing 56 (FIG. 1) of the system 50 (FIG. 1), though, on a much smaller scale. The actuating plate 200 is configured to interact with the pipetting head 192 as described in detail below.

The cage 190 further includes a block 202 that extends downwardly away from the housing 194 and is configured to receive the pipetting head 192. For example, the block 202 may include a shelf 204 for interfacing with a shoulder 206 of the pipetting head 192; however, other methods of interfacing a matrix-style pipetting head 192 with a cage 190 may also be used.

The matrix-style pipetting head 192 may generally include any air-displacement or positive displacement pipetting head structure having any number of channels, though the number of channels will conventionally range from 96 to 384 or more. The channels are generally arranged in a two-dimensional array. As illustrated, the pipetting head 192 has a body portion 208, a top plate 210, and a bottom plate 212, where the lateral dimension of the body portion 208 is illustrated as being smaller than the lateral dimension of at least the top plate 210 to define the shoulders 206.

The body portion 208 contains a two-dimensional array of microtubes 214, each receiving a piston 216 that extends therethrough. A top portion of each piston 216 is embedded into a plunger plate 218 so that all pistons 216 are actuated in unison to deliver metered quantities of fluid to a multi-well tray 224 (FIG. 1), a reservoir, or any other suitable labware.

Figure 8B:
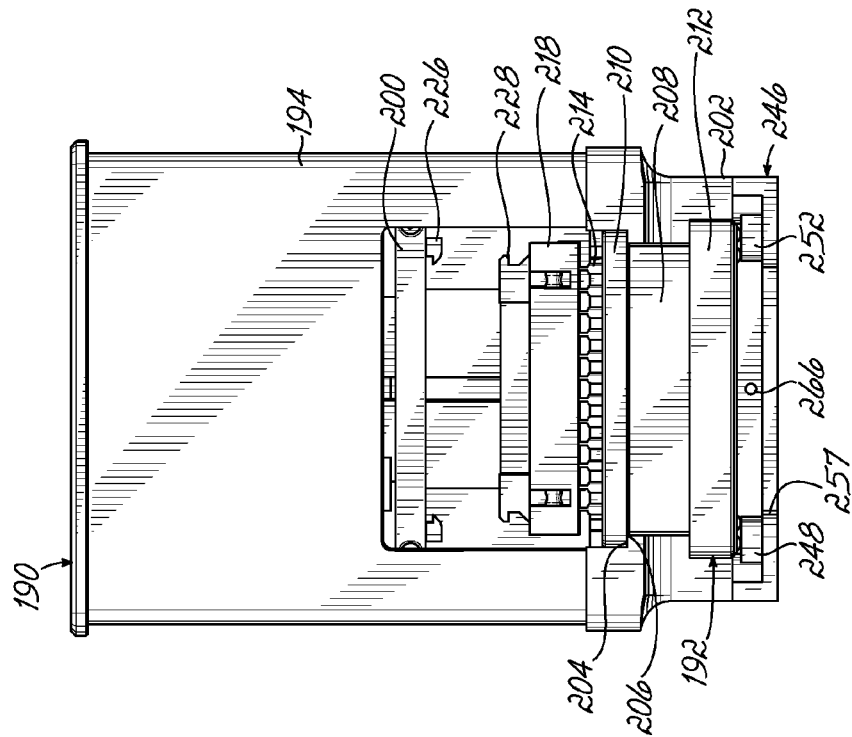
FIG. 8B is a front elevational view of the cage and matrix-style pipetting head as shown in FIG. 8A.
Figure 8A:
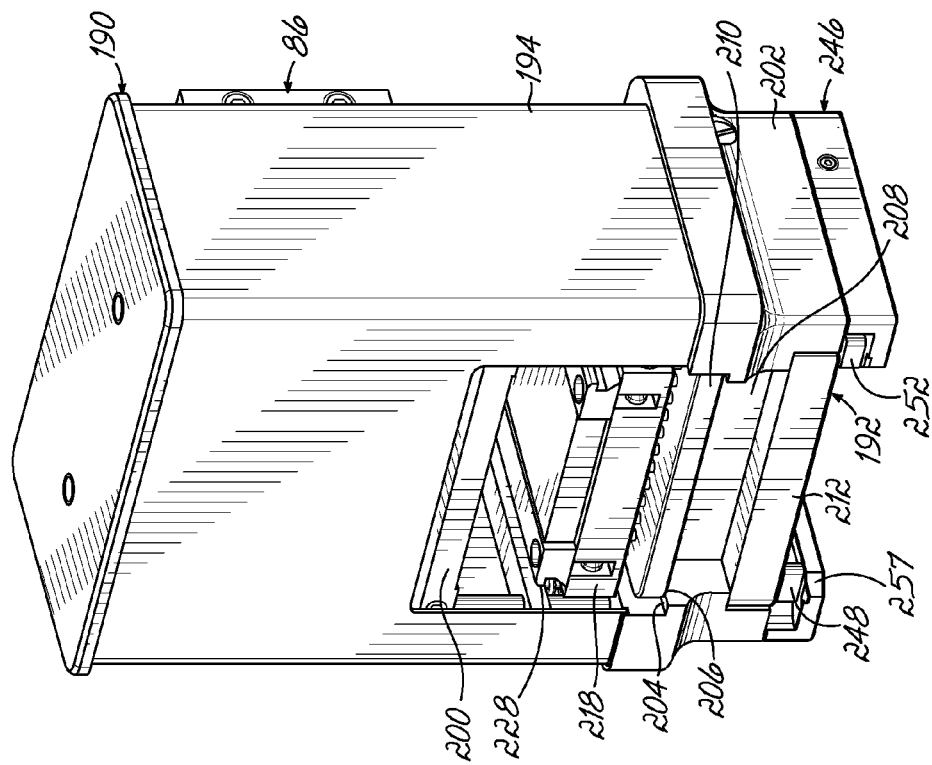
FIG. 8A is a perspective view of the matrix-style pipetting head loaded into the cage.

One method of coupling the pipetting head 192 to the cage 190 is described with reference to FIGS. 8A-9C. In FIGS. 8A and 8B, the pipetting head 192 is fully inserted into the block 202 of the cage 190 by sliding the shoulder 206 along the shelf 204 of the block 202. A ball plunger 220 of the block 202 mates with an alignment hole 222 of the pipetting head 192 when the pipetting head 192 is properly and fully positioned within the block 202. The ball plunger 220 therefore facilitates consistent assembly of the cage 190.

Specifically referring now to FIGS. 9A-9C, with continued reference to FIGS. 8A and 8B, the actuating plate 200 of the cage 190 is lowered to couple the pipetting head 192 to the cage 190 via the piston plate 218. In the FIG. 9A, the actuator plate 200 of the cage 190 is lowered to a position that is above the piston plate 218 of the pipetting head 192. In this position, a clip 226 of the actuator plate 200 is adjacent to a hook 228 of the piston plate 218. The clip 226 and the hook 228 are keyed with corresponding shapes to facilitate engagement and corresponding angled outer surfaces 230, 232, respectively, to facilitate the engagement.

As the actuator plate 200 continues to be lowered toward the piston plate 218, the angled outer surface 230 of the clip 226 is biased laterally, as shown in FIG. 9B, and slides along the angled outer surface 232 of the hook 228 until the clip 226 engages the hook 228, as shown in FIG. 9C. Vertical translation of the actuator plate 200 therefore vertically translates the piston plate 218 and may aspirate and/or dispense fluid as appropriate.

Figure 10:
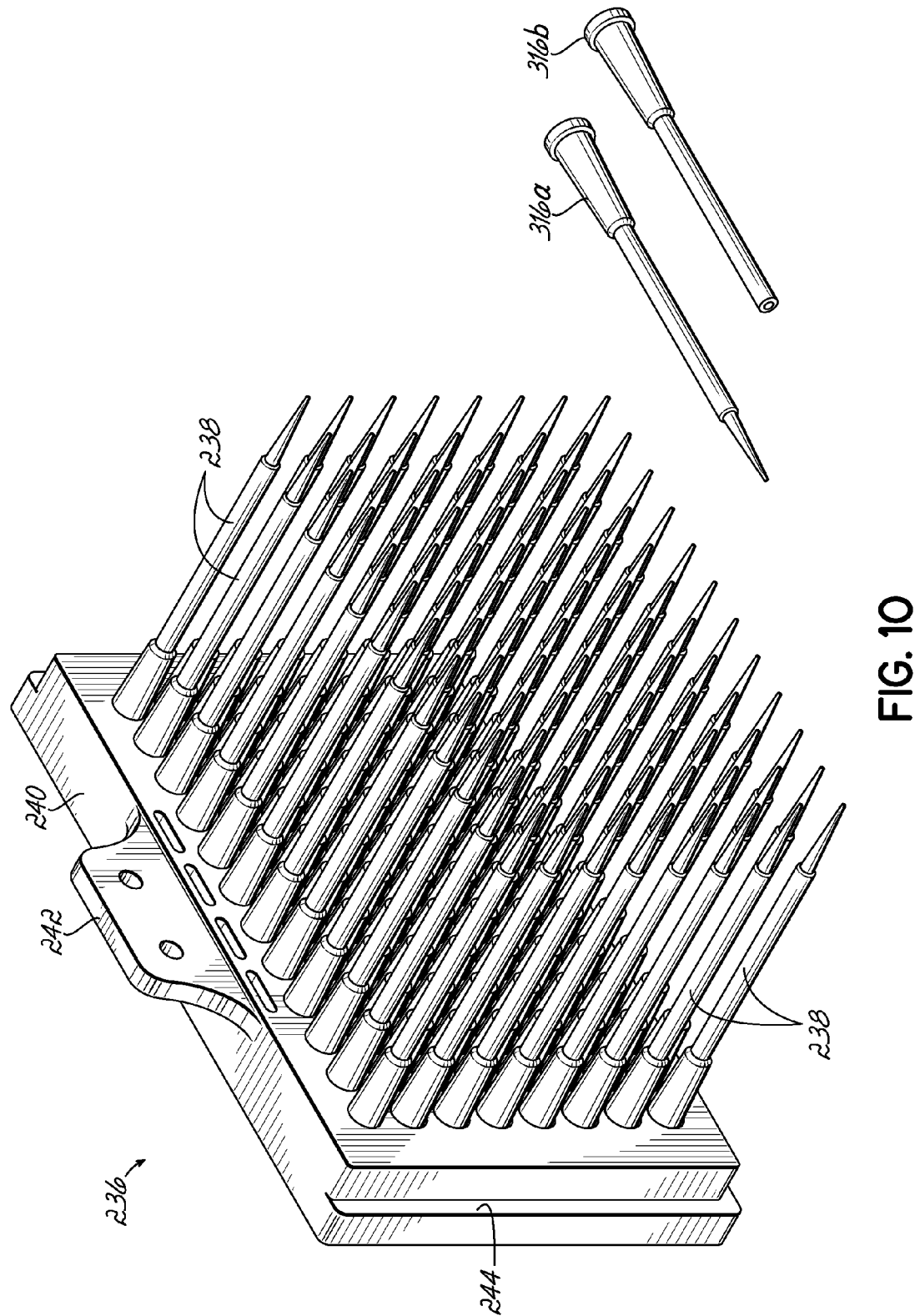
FIG. 10 is a perspective view of a magazine of a matrix-array of pipetting tips.

With the pipetting head 192 operably secured within the cage 190, the cage 190 is ready to receive a magazine of disposable tips for fluid transfer. FIG. 10 illustrates one suitable embodiment of a magazine 236, such as the commercially-available Matrix D.A.R.T.S® (Disposable Automation Research Tips) tips (Thermo Fisher Scientific); however, other disposable tips may also be used. As shown, the magazine 236 includes an array of pipetting tips 238, wherein the number of pipetting tips 238 comprising the array is equal to the number of microtubules 214 (FIG. 6) of the pipetting head 192. The pipette tips 238 may vary in size and shape, and, for example, may cover volumes ranging from 0.5 μL to 30 μL or 5.0 μL to 300 μL for the 96-array configuration and 0.5 μL to 30 μL or 1.0 μL to 100 μL in the 384-array configuration. Each pipetting tip 238 includes a distally-tapering design with a lumen extending therethrough, as would be known to those of ordinary skill in the art. Each pipetting tip 238 also extends away from a support body 240 and, in some embodiments, may be constructed as a unitary structure with the support body 240. The support body 240 may further include a tab 242 for ease of handling when removing the magazine 236 from the block 202 and a shelf 244 configured engaging a magazine clip 246 of the block 202.

Figure 11:
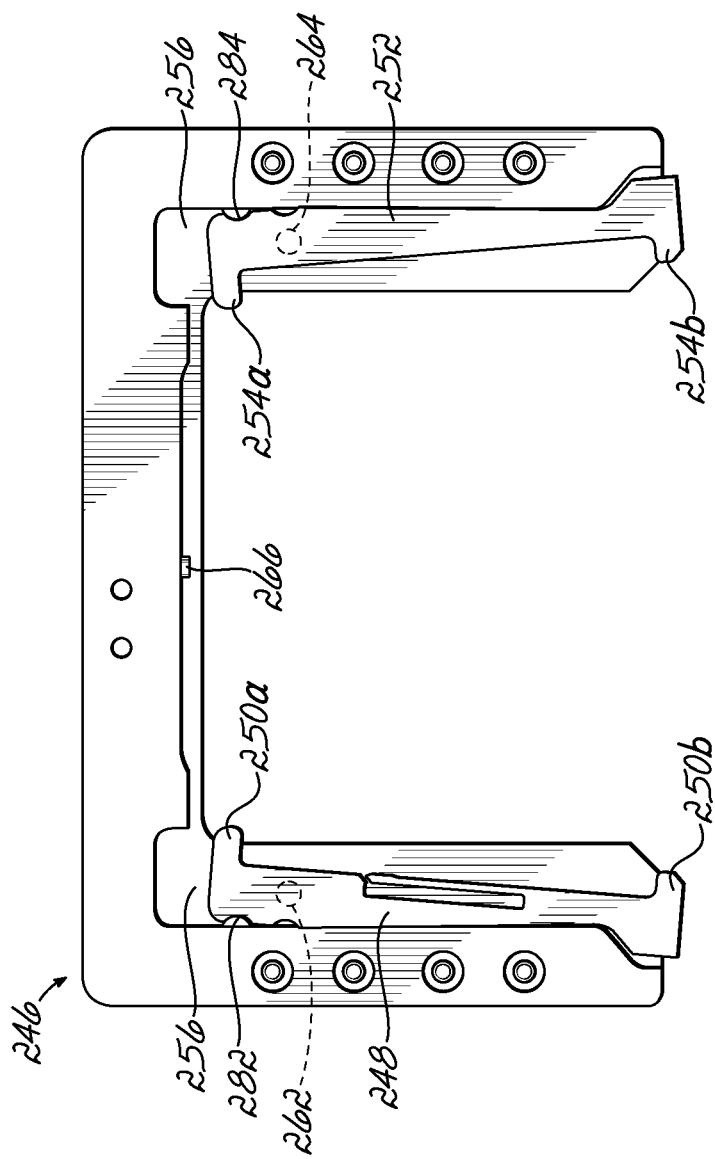
FIG. 11 is a top view of a magazine clip of the cage.
Figure 12:
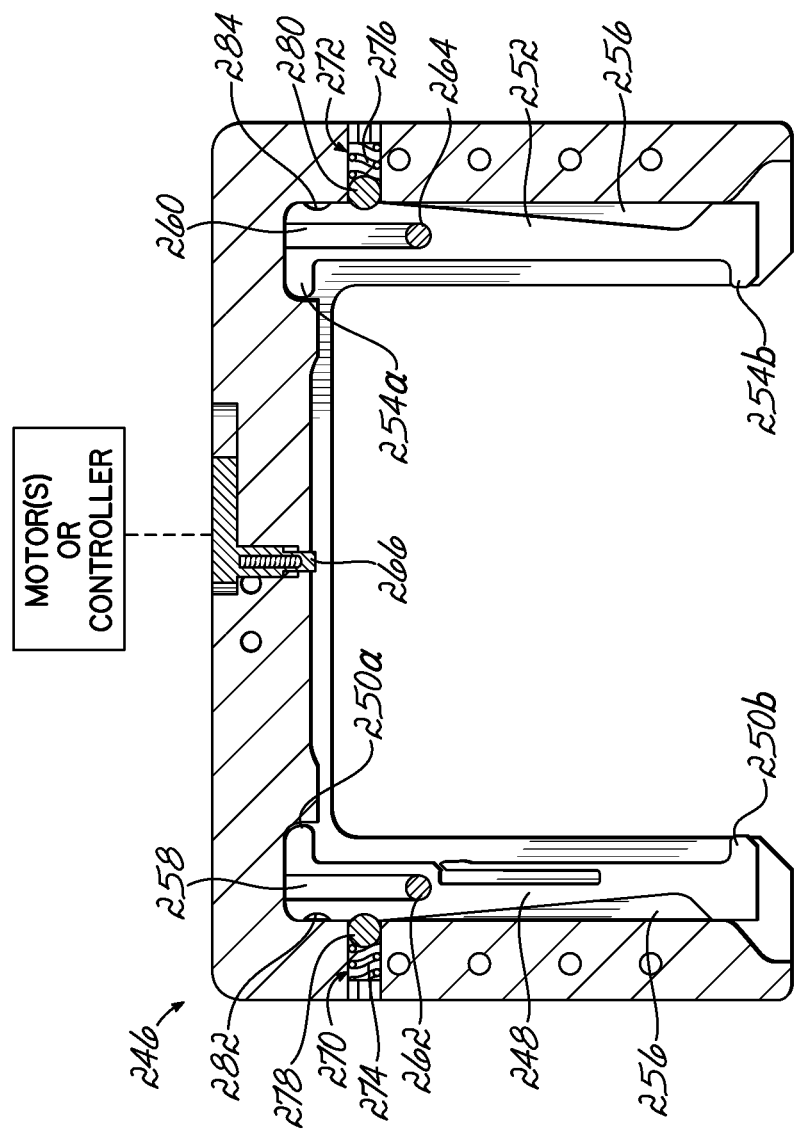
FIG. 12 is a cross-sectional view of the magazine clip of FIG. 11.

FIGS. 11 and 12 illustrate the magazine clip 246 in greater detail. The magazine clip 246 includes a first arm 248 having a first pair of tabs 250a, 250b and a second arm 252 having a second pair of tabs 254a, 254b. Each of the arms 248, 252 resides in a slot 256 on opposing inner surfaces of the block 202 (FIG. 6). Accordingly, and as the magazine 236 (FIG. 10) slides into the magazine clip 246 with the shelf 244 (FIG. 10) sliding along a lower base 257, the tabs 250a, 250b, 254a, 254b engage and surround the lateral ends of the shelf 244 (FIG. 10) of the magazine 236 (FIG. 10).

When the magazine 236 (FIG. 10) is fully inserted, the arms 248, 252 slide rearwardly within the slot 256, as shown in the cross-sectional view of FIG. 12. To maintain the alignment of the magazine clip 246 within the block 202 (FIG. 6), each arm 248, 252 may each include a slot 258, 260 herein that slidably receives a pin 262, 264. In this way, the arms 248, 252 may only slide in such a manner that the pins 262, 264 remain within the slots 258, 260.

A sensor 266 may be positioned in the rear of the magazine clip 246 to provide an electronic signal associated with a feedback control to one or more motors (not shown) or a controller (not shown) of the automated liquid handling device 50 (FIG. 1) to prevent the user from operating a misaligned magazine 236. More particularly, the sensor 266 detects the proximity of the magazine 236 with respect to the magazine clip 246. If the magazine 236 is not fully loaded within the magazine clip 246, as detected by the sensor 266, then a feedback control mechanism of the controller (not shown) limits the operation of one or more motors (not shown) of the system 50 (FIG. 1). In this way, the controller (not shown) and feedback control mechanism prevents the user from operating the automated liquid handling device 50 (FIG. 1) with a misaligned pipetting head 192 (FIG. 6) with respect to the cage 190 (via a pipetting head sensor 268 in the rear wall of the cage 190) or a misaligned magazine 236 with respect to the pipetting head 192 (via the magazine sensor 266).

Figure 13:
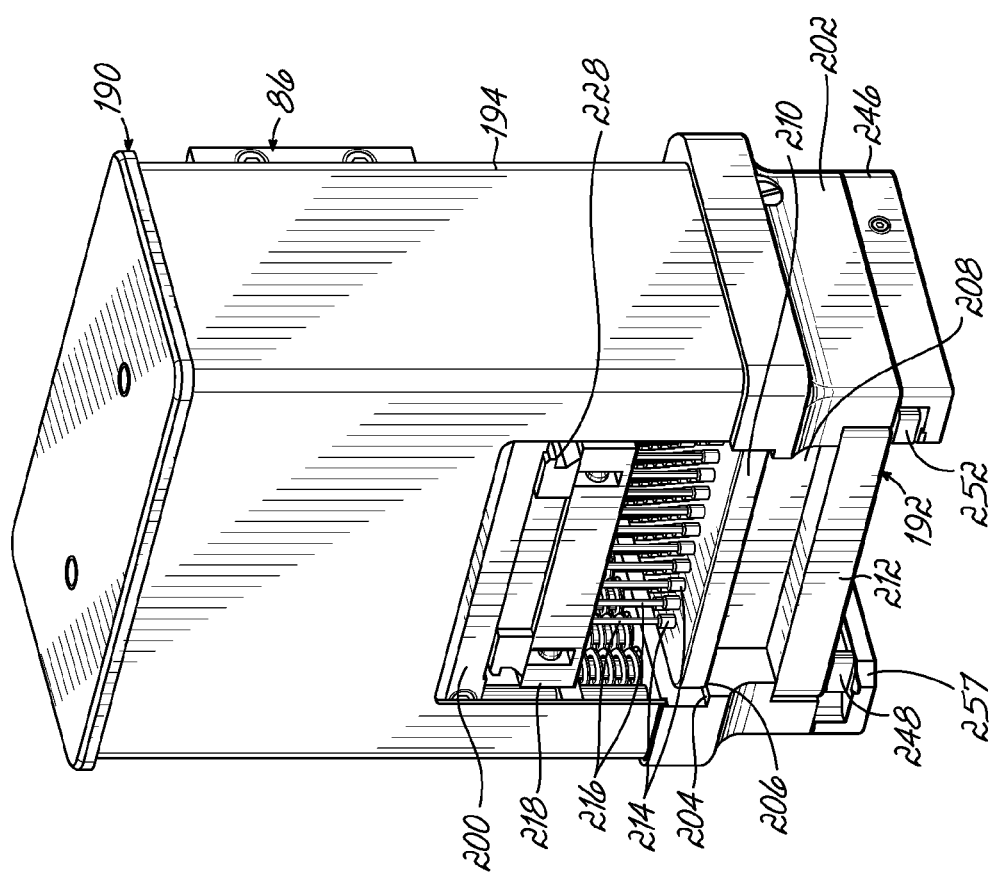
FIG. 13 is a perspective view of the matrix-style pipetting head with a magazine of pipetting tips loaded into the cage.

With reference now to FIG. 13 where the actuator and piston plates 200, 218 are engaged and the magazine 236 is properly installed into the pipetting head 192, the motor (not shown) of the cage 190 may be operated so as to elevate the actuator plate 200 within the cage 190. Because the clip 226 engages the hook 228, elevating the actuator plate 200 also lifts the piston plate 218 of the pipetting head 192 and pistons 216 coupled thereto to aspirate fluid into the microtubules 214, as was as described in U.S. Pat. No. 6,982,063. Lowering the actuator plate 200 likewise lowers the piston plate 218 and the pistons 216 to dispense the fluid from the microtubules 214.

When the user desires to change the liquid handling system 58, for example, switching between a 96-matrix pipetting head to a 384-matrix pipetting head, the user operates the motor (not shown) of the cage 190 to lower the actuator plate 200 with the piston plate 218 until the piston plate 218 is positioned at rest relative to the top plate 210 of the pipetting head 192. The magazine 236 is removed with the user pulling on the tab 242 to slide the magazine 236 outwardly from the pipetting head 192 along the lower base 257. Because each arm 248, 252 of the magazine clip 246 is operably associated with a biased ball-joint 270, 272, withdrawing the magazine 236 from the pipetting head 192 does not remove the magazine clip 246 from the block 202. More specifically, each ball-joint 270, 272 includes a spring 274, 276 biasing a ball bearing 278, 280 laterally inwardly and into the slot 256. As the magazine 236 is withdrawn from the magazine clip 246 and the arms 248, 252 are pulled forwardly within the slot 256, the springs 274, 276 outwardly bias the respective ball bearings 278, 280 until each ball bearing 278, 280 is received within a groove 282, 284 in each respective arm 248, 250. Once the ball bearing 278, 280 engages the respective groove 282, 284, the arms 248, 250 are prevented from being withdrawn from the block 202.

With the magazine 236 removed, the user may again activate the motor (not shown) to further lower the actuator plate 200 beyond the position that is illustrated in FIG. 9C. This continued motion releases the clip 226 from the hook 228, which resultantly releases the pipetting head 192 from the cage 190. The user may then slide the pipetting head 192 out of the block 202 along the shelf 204.

In some circumstances the user may desire to utilize a smaller liquid handling system 58, for example, a single pipette (not shown) or linear array of pipetting channels, such as an 8-channel pipetting head 286 (FIG. 1) or a 12-channel pipetting head 292 (FIG. 1). FIGS. 14-20 illustrate an adaptor cage 290 that is configured to receive a single or linear-array pipetting head 286, 292 (FIG. 1) for use in the automated liquid handling system 50 (FIG. 1).

Turning to FIG. 14, the adaptor cage 290 for receiving the pipetting head 286, 292 is shown in greater detail. A rear surface 294 of the adaptor cage 290 includes a recess 296 in which the adaptor plate 86 is mounted. By recessing the adaptor plate 86 away from the rear surface 294, the recess 296 may receive the support block 84 while the rear surface 294 contacts, and vertically-translates along, the rear wall 60 (FIG. 5A) of the upper housing 56 (FIG. 1) as shown in FIG. 15.

In the illustrative embodiment, the adaptor cage 290 has a wedge-like shape extending forward of the rear surface 294 with a substantially horizontal upper surface 298 and forwardly-tapering sidewalls 300; however, it would be readily understood that the adaptor cage 290 is not limited to the particular illustrated shape. The wedge-like shape defines a large volume end 302 configured to house and support one or more of (though none are specifically shown) an x-direction motor, a series of pulleys operably associated with the x-direction motor, a y-direction motor, and a series of pulleys operably associated with the y-direction motor. Each motor and associated series of pulleys may be similar to the motor (not shown) and pulleys 152 that are described above. The motors, pulleys, belts within the large volume end 302 are configured to move a pipettor block 304 and ejector plate 306, which extend downwardly from the adaptor cage 290, in the x- and y-directions, respectively. The pipettor block 304 is configured to receive the pipetting head 286, 292 so that movement of the pipettor block 304 also moves the pipetting head 286, 292 in the x- and/or y-directions and into alignment with the multi-well tray 224 (FIG. 1), the reservoir, or any other labware that is known to those of ordinary skill in the art.

The large volume end 302 may also include a z-direction motor (not shown) with a series of pulleys and a belt (not shown), to operate the pipetting head 286, 292 so as to aspirate and/or dispense a fluid, as described in detail below.

Figure 16:
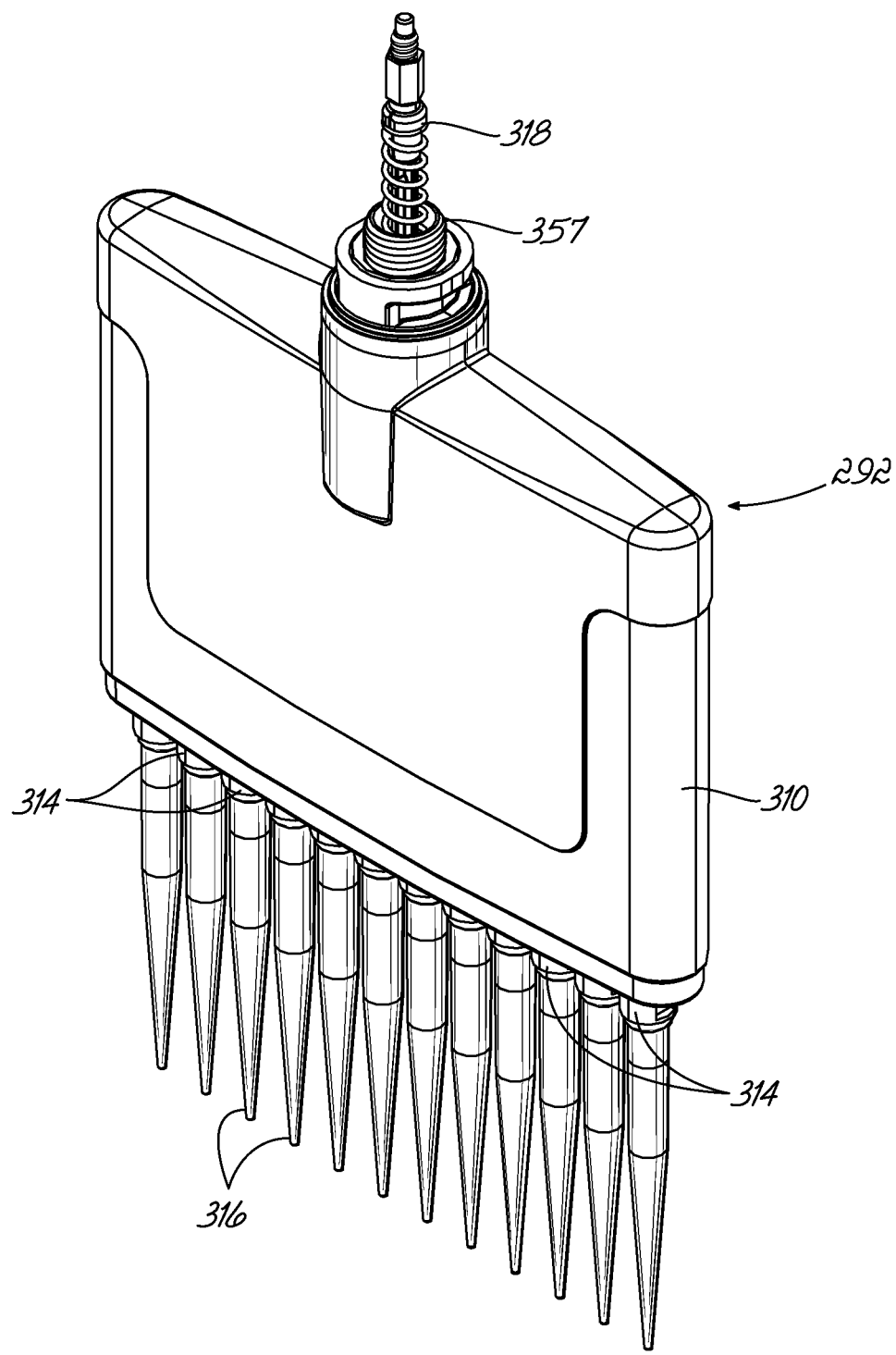
FIG. 16 is a perspective view of a 12-channel pipetting head with disposable pipetting tips.

Turning now to FIG. 16, where one exemplary embodiment of the 12-channel linear-array pipetting head 292 is shown and briefly described. The pipetting head 292 includes a housing 310 supporting a linear array of tubes (not shown) therein where the number of tubes is equal to the number of channels comprising the linear array. Each tube (not shown) includes a distal hub 314 that is sized and shaped to receive a suitably sized and shaped pipetting tip 316a, 316b. Two embodiments of the pipetting tips 316a, 316b are shown in still greater detail in FIG. 10. In particular, the pipetting tips 316a may be constructed with tapered shape, similar to the pipetting tip 238 described previously, or may be truncated. Still other shapes of pipetting tips 316 are known and may be implemented with the liquid handling system 58 (FIG. 1) as desired.

Returning again to FIG. 16, a dispenser mechanism (not shown) within the housing 310 is operably coupled to each of the tubes (not shown) for actuating the aspirating fluid into and dispensing fluid from the pipetting tips 316. One exemplary dispenser mechanism, such as the plunger described in U.S. Pat. No. 7,284,454, the disclosure of which is incorporated herein by reference in its entirety. The plunger (not shown) is operably coupled to an extension 318 that projects upwardly from the plunger (not shown) and outwardly from the housing 310 so as to be operably coupled to the pipetting head 292 (FIG. 10).

Figure 17A:
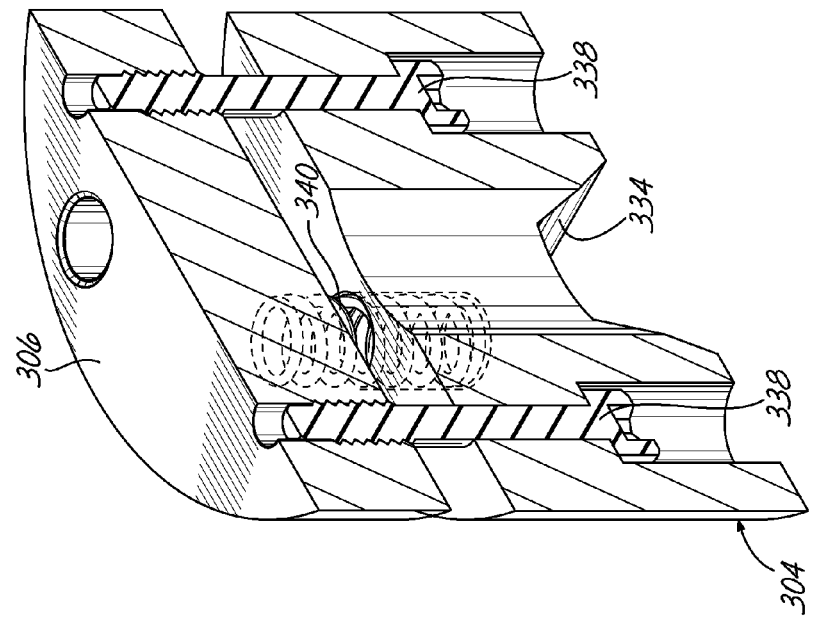
FIG. 17A is a cross-sectional view taken along the line 17A-17A in FIG. 17.
Figure 17:
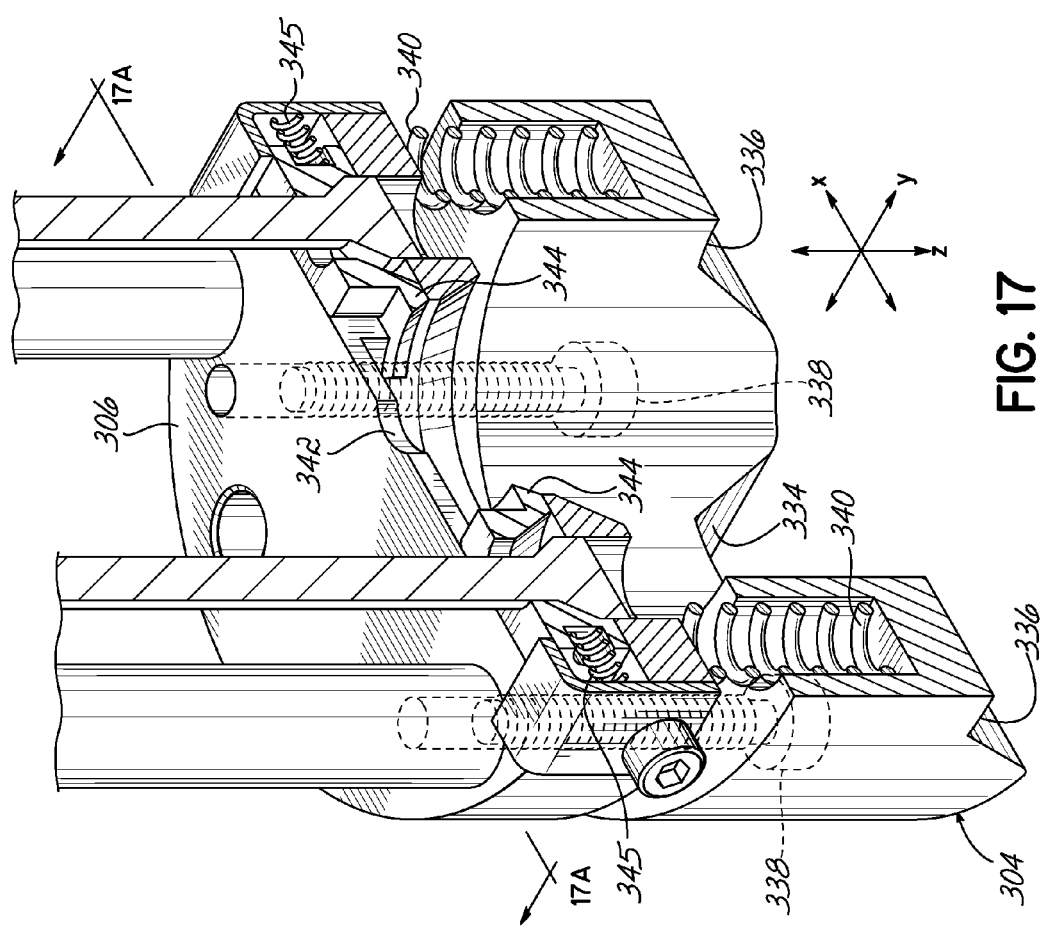
FIG. 17 is a cross-sectional view through an ejector plate and pipettor block of the adaptor cage of FIG. 14.

Turning now to FIGS. 17 and 17A, the details of the pipettor block 304 and the ejector plate 306 are described in greater detail. The pipettor block 304 includes two troughs 334, 336, one in each of the x-direction and the y-direction, respectively. The troughs 334, 336 are shaped and sized to accommodate the housing 310 of the pipetting head 292 (FIG. 16). For example, the troughs 334, 336 may be configured so that the trough 334 extending in the x-direction receives the 12-channel pipetting head 292 (FIG. 16) and the trough 336 extending in the y-direction receives the 8-channel pipetting head 286 (FIG. 1). Generally, the direction of the trough 334, 336 is selected to most efficiently interact with the multi-well arrangements of trays 224 (FIG. 1) or other labware. For example, some labware includes a plurality of wells that is arranged into 8 rows and 12 columns (96 array), 16 rows and 24 columns (384 array), or 24 rows and 64 columns (1536 array) where the rows are in the y-direction and columns are in the x-direction. Therefore, the selection of the 8-channel or 12 channel pipetting head 286, 292 may be based, at least in part, on the most efficient manner of transferring liquid with respect to the labware.

The pipettor block 304 is mounted to the ejection plate 306 by shoulder bolts 338 with one or more springs 340 also extending between for biasing the pipettor block 304 away from the ejection plate 306. The pipettor block 304 and the ejector plate 306 include a centrally-disposed bore 342 that is configured to receive the extension 318 (FIG. 16) of the pipetting head 292 (FIG. 16). One or more retractable ears 344, biased toward the bore 342 by a spring 345, engage the extension 318 thereby coupling the pipetting head 292 to the pipettor block 304 while also providing a quick release mechanism.

As the pipetting head 292 is inserted into the pipettor block 304, the extension 318 is directed into the centrally-disposed bore 342 and the housing 310 into the appropriate trough 334, 336. When the pipetting head 292 is properly aligned and inserted, the retractable ears 344 engage and retain the housing 310 in position. Because the pipettor block 304 is biased by the one or more springs 340 away from the ejector plate 306, the pipetting head 292 will fit snuggly within the trough 334, 336 and is locked into position. This reduces inadvertent angular or rotational movement of the pipetting head 292 once it is positioned within the pipettor block 304.

When the extension 318 is fully extended through the centrally-disposed bore 342, it is then operably associated with a crash prevention device 346, one exemplary embodiment of which is shown in FIGS. 18A-20. The crash prevention device 346 includes a block housing 348, an insert 350, and a compression spring 352 within the block housing 348 for biasing the insert 350 outwardly. One or more couplers 354 extend from the insert 350 through the block housing 348 to a ring 356. The ring 356, block housing 348, spring 352, and insert 350 all include a centrally-disposed bore 358 that is collinear with the centrally-disposed port 342 and to receive the extension 318 of the pipetting head 292 (FIG. 16). Indeed, in the assembled embodiment shown in FIG. 20, the extension 318 further includes a threaded sleeve thereon 357 that is configured to engage an inner threaded surface 359 of the insert 350.

Figure 18B:
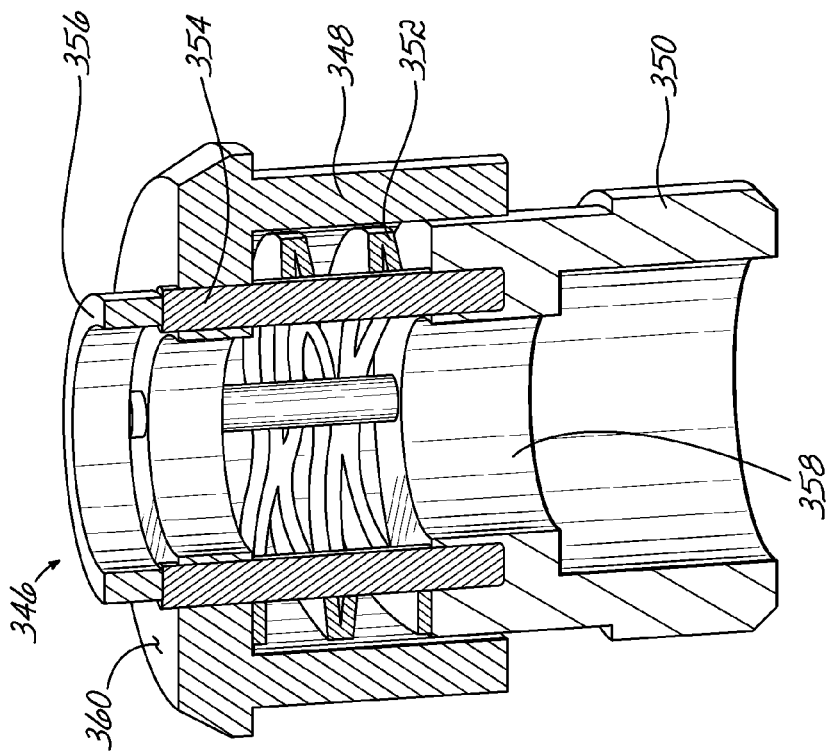
Figure 18A:
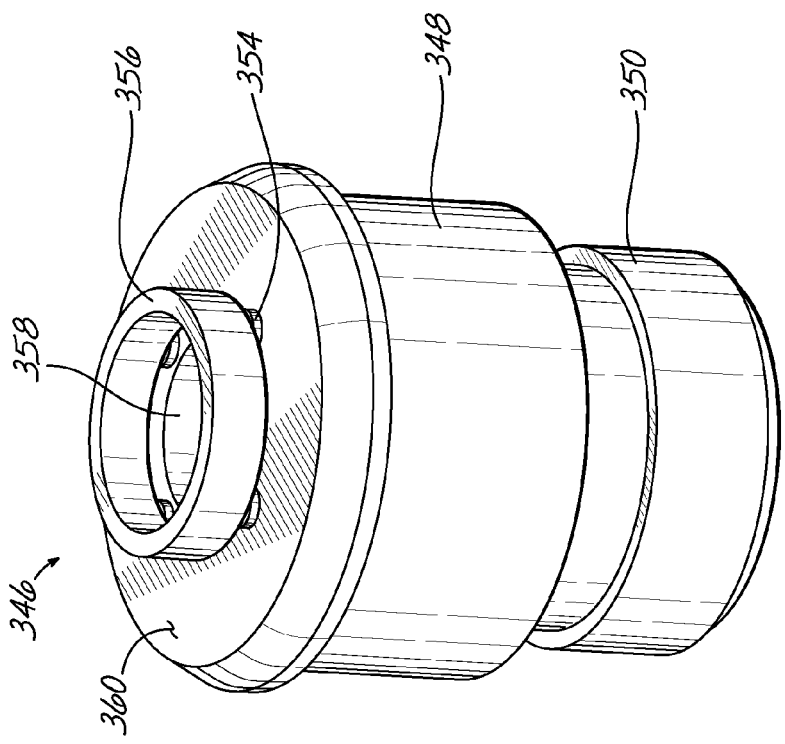

In FIG. 18A, when the bias spring 352 of the crash prevention device 346 is in a first, relaxed state, the insert 350 is extended within the block housing 348, and the ring 356 resides along a top surface 360 of the block housing 348. FIG. 18B illustrates the same position in cross-section. When the insert 350 is forced into the block housing 348, as shown in FIG. 19A, the spring 352 is compressed. Resultantly, the couplers 354 force the ring 356 upwardly such that it is spaced away from the top surface 360 of the block housing 348. The internal structure of this position is shown in cross-section in FIG. 19B.

Figure 20:
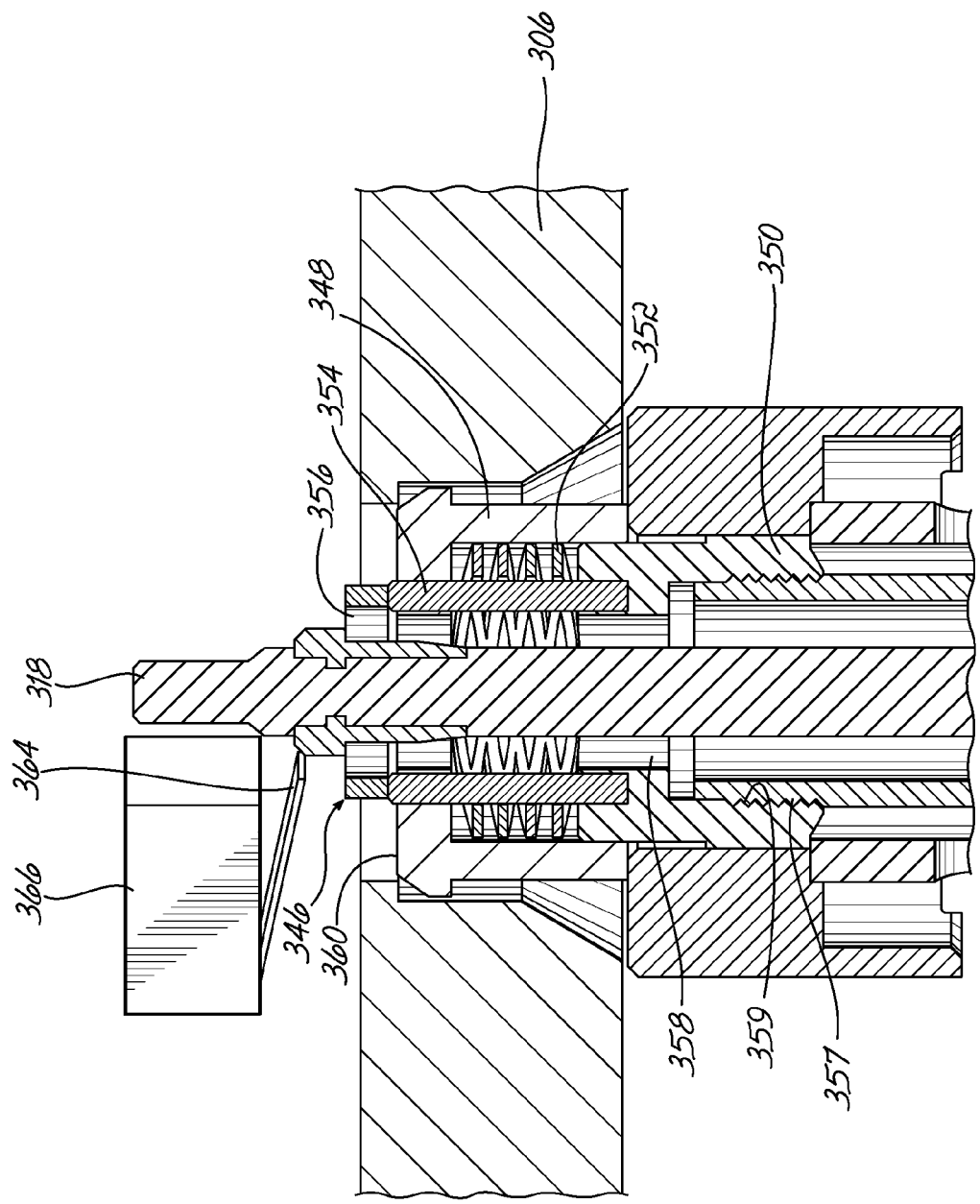
FIG. 20 is a cross-sectional view of an extension of the 12-channel pipetting head of FIG. 16 extending through the pipette and ejector plate to activate the crash prevention device of FIG. 18A.

In operation, as shown in FIG. 20 with reference to FIGS. 15-17, as the user operates the motors (not shown) so as to translate the adaptor cage 290 downwardly along the rear wall 60, the pipetting tips 316 may engage the tray 224 (FIG. 1), the matrix of wells, the reservoir, or any other labware residing in or on a stage 362 (FIG. 21) within the lower housing 52 (FIG. 1), and the pipette head 292 is prevented from further motion. However, the motor (not shown) may continue to operate and further force the adaptor cage 290 downward. This downward force by the adaptor cage 290 translates upwardly through the pipetting head 292, which being operably coupled to the crash prevention device 346, creates an upwardly-directed force on the insert 350. As the insert 350 moves upwardly against the bias of the springs 352, the couplers 354 and the ring 356 also move upwardly. The ring 356, once displaced from a top surface 360 of the block housing 348, contacts an arm 364 of a switch 366; continued upward movement of the ring 356 displaces the arm 364 and activates the switch 366, which in turn terminates operation of the motor (not shown) and the downward movement of the pipetting head 292. It would be understood by those of ordinary skill in the art that the switch 366 could alternatively be a sensor, a microswitch, or other like devices.

Turning now to the details of the stage, and in particular, a first embodiment of the stage 362 is shown and described with reference to FIGS. 21A-22B. The stage 362 includes a tray support surface 378, which may include one or more dividers 380 to separate the tray support surface 378 into two or more areas 376a, 376b for securing two or more trays 224 (FIG. 1) thereon. The stage 362 is coupled to the bottom surface 382 of the work space 54 (FIG. 1) by a stage brace 384. The stage brace 384 extends upwardly through a first opening 386 in the bottom surface 382.

If so desired, the lower housing 52 (FIG. 1) may further include a bar code reader 416 (FIG. 1) or other like device positioned within the work space 54 (FIG. 1) and in close proximity to the stage 362. The bar code reader 416 (FIG. 1) is configured to scan or detect a bar code, a radiofrequency identification tag ("RFID"), or other similar mark on one or more surfaces of the trays 224 (FIG. 1), as is conventional.

The stage 362 includes a support leg 390 extending away from the bottom of the stage 362 and poised to be received by the stage brace 384. One or more fixation devices 392, such as screws, bolts, dowels, rods, etc., may then be used to secure the stage 362 to the support leg 390.

Figure 22B:
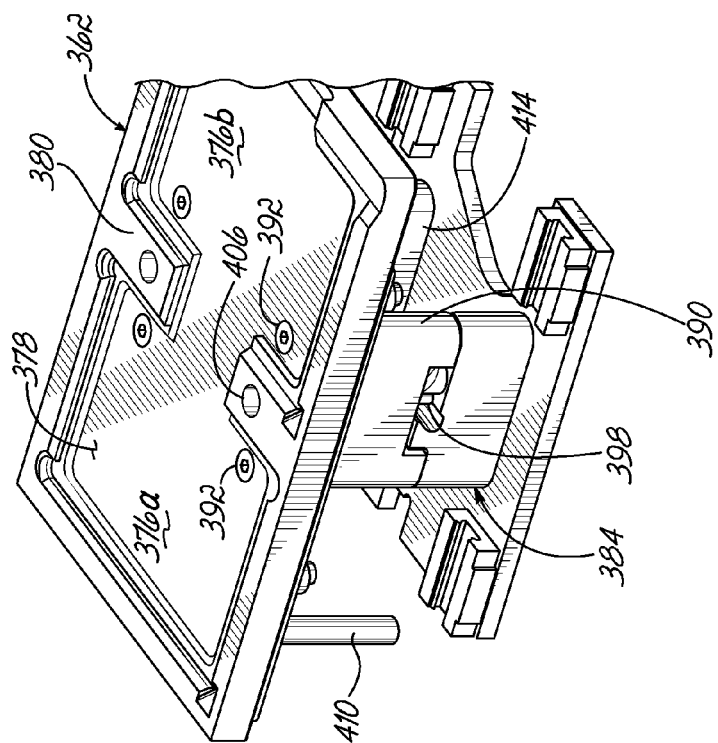
Figure 22A:
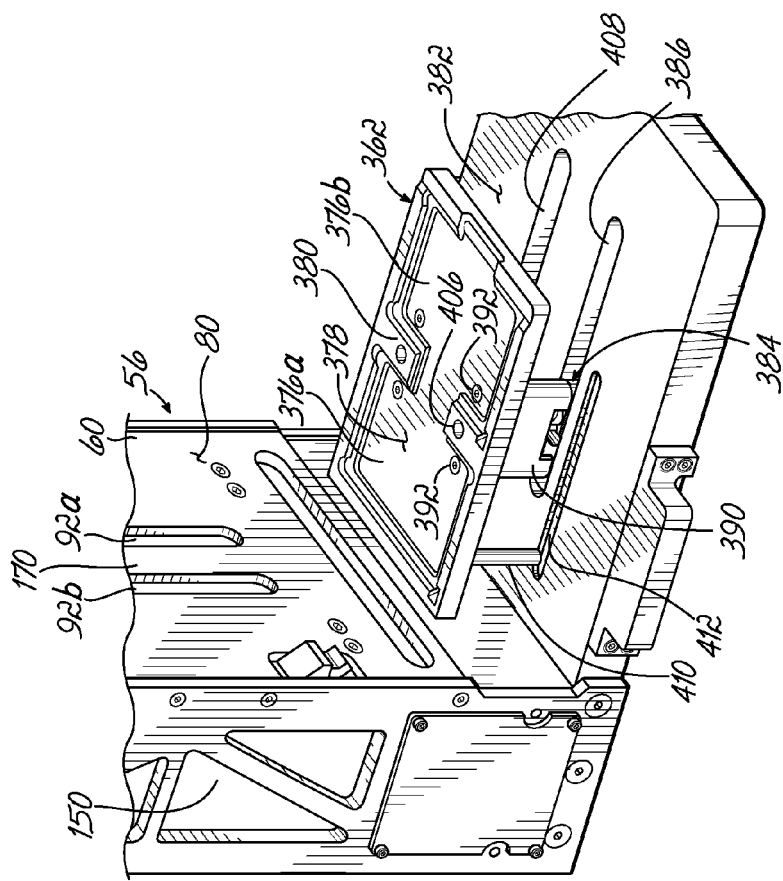
Figure 22C:
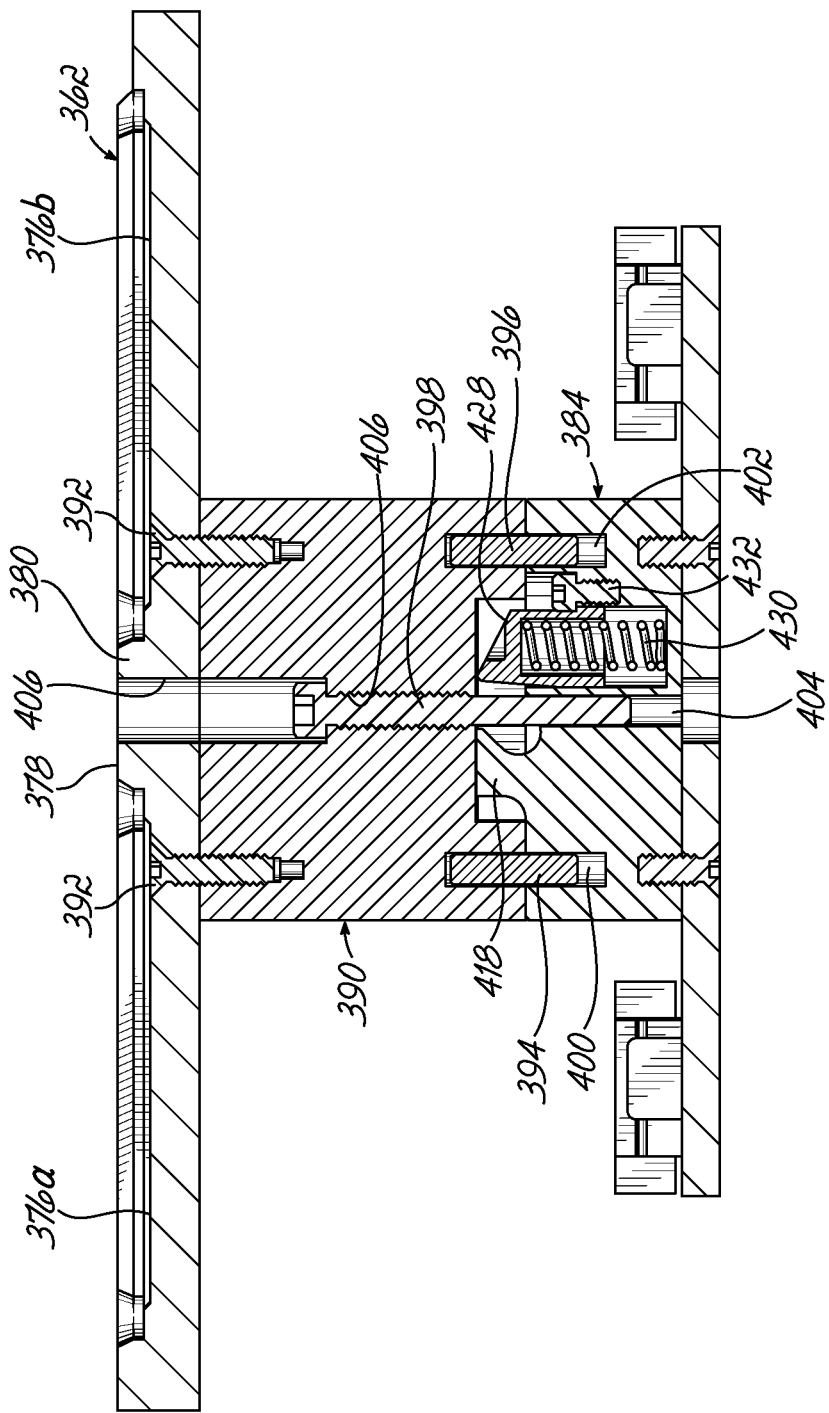
FIG. 22C is a cross-sectional view through tray supporting surface as it is coupled to the bottom surface of the lower housing.

The support leg 390 includes two dowels 394, 396 and a central fixture device 398, for example, a screw, which extend into holes 400, 402, 404 of the stage brace 384, respectively, and in a manner described below. After the dowels 394, 396 of the support leg 390 are directed into the holes 400, 402 of the stage brace 384, the screw 398 may extend downwardly through a threaded hole 406 in the support leg 390 and enters the designated hole 404 of the stage brace 384. The stage 362 may then be secured to the stage brace 384 by tightening the screw 398 as shown in FIG. 22C.

Though not shown, the stage 362 may further include a second support leg (not shown) that is similar to the support leg 390 to be coupled to a second stage brace 414 extending upwardly from a second opening 408 formed in the bottom surface 382 of the lower housing 52 (FIG. 1). However, only one support leg 390 is needed to secure the stage 362 to the housing 52.

In some embodiments, though not specifically shown, the support leg 390 and stage brace 384 may be operably coupled with a motor (not shown) to translate the stage 362 in the y-direction along the bottom surface 382 of the lower housing 52 (FIG. 1). Accordingly, a guide 410 may extend downwardly from the stage 362 to ride along a guide groove 412 in the bottom surface 382 of the lower housing 52 (FIG. 1). Movement of the stage 362 is not necessary.

Figure 23B:
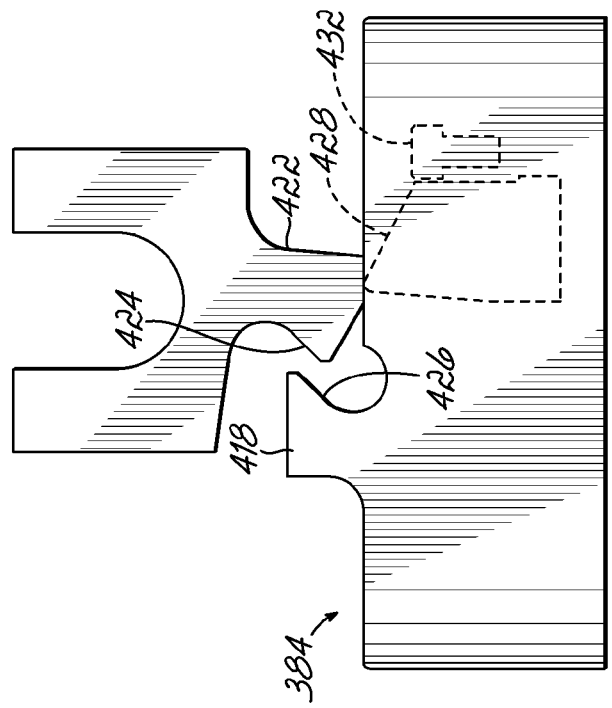
FIG. 23B is an assembled side elevational view of the support hook as it is being coupled to the bottom surface of the lower housing.
Figure 23A:
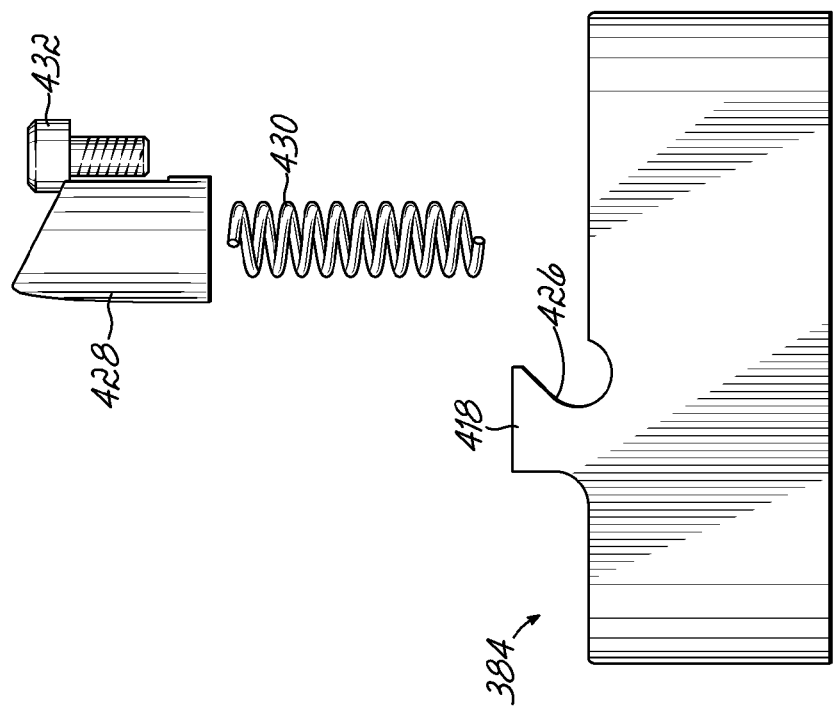
FIG. 23A is an exploded disassembled side elevational view of an alternate embodiment of a support hook for coupling an adjustable stage to the bottom surface of the lower housing.
Figure 24A:
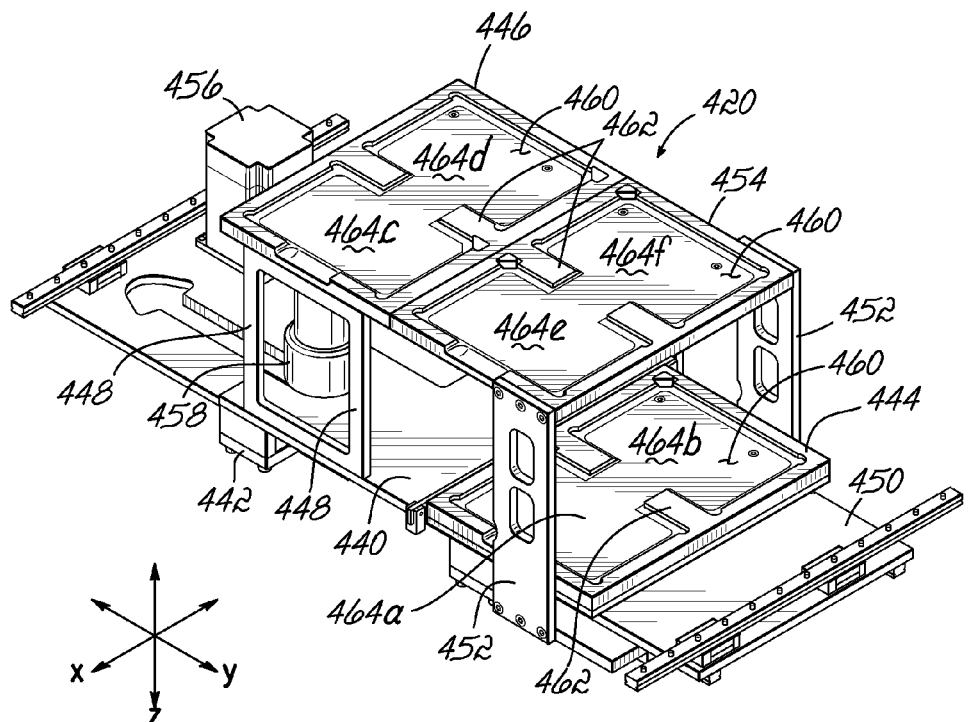
FIG. 24A is a perspective view of an adjustable stage configured to support four trays.
Figure 24B:
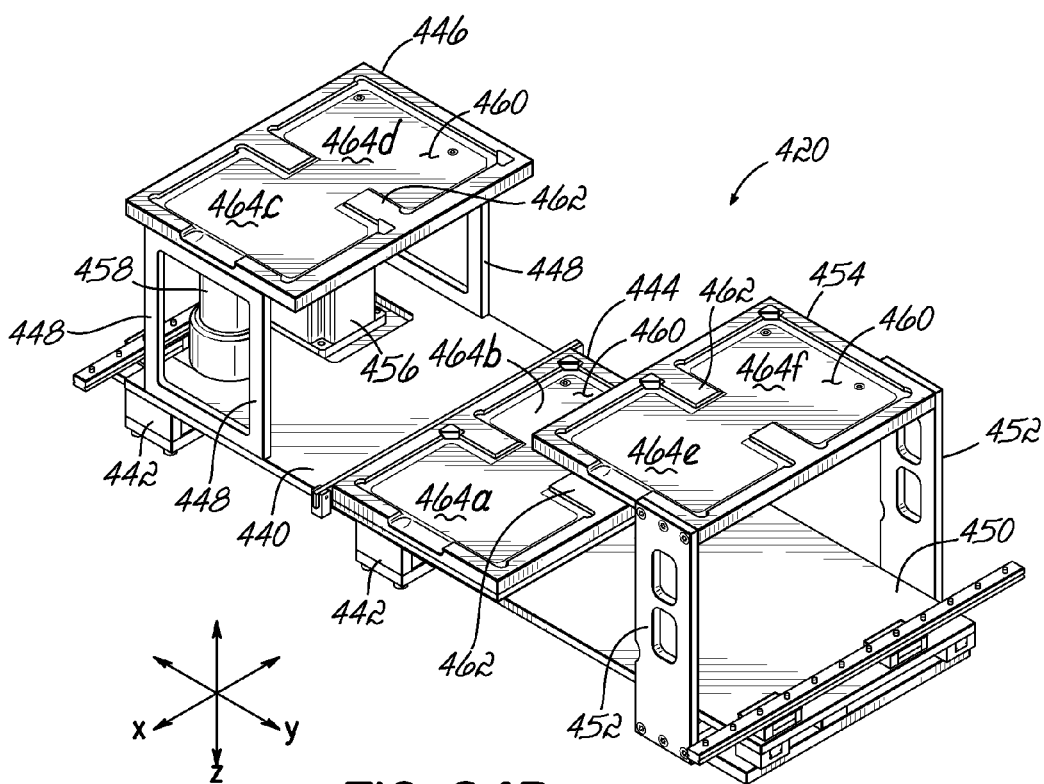
FIG. 24B is a perspective view of the adjustable stage of FIG. 24A expanded to support six trays.
Figure 25A:
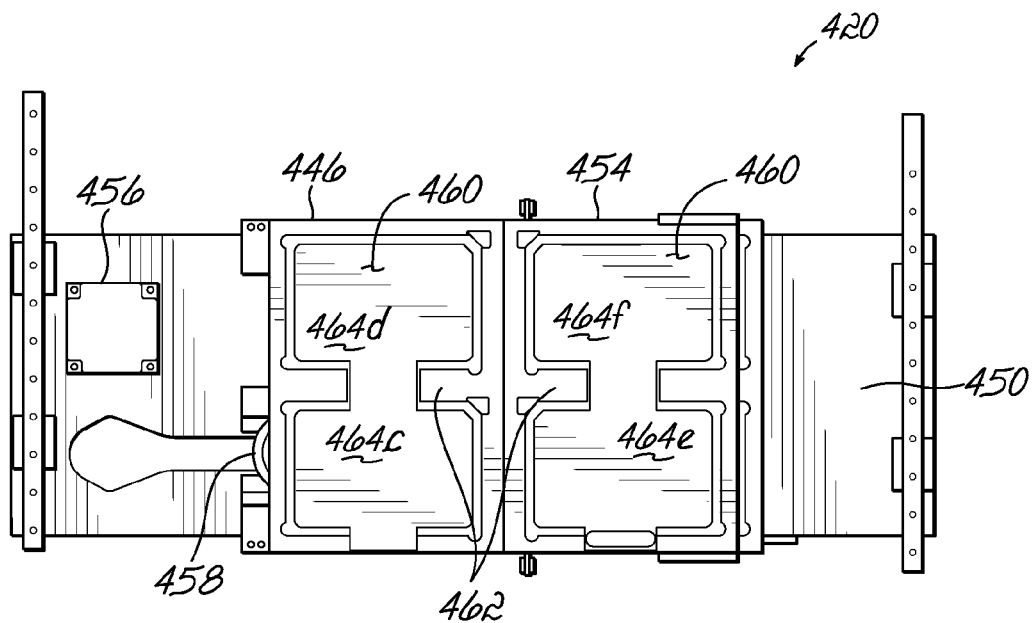
FIG. 25A is a top view of the adjustable stage as shown in FIG. 24A.
Figure 25B:
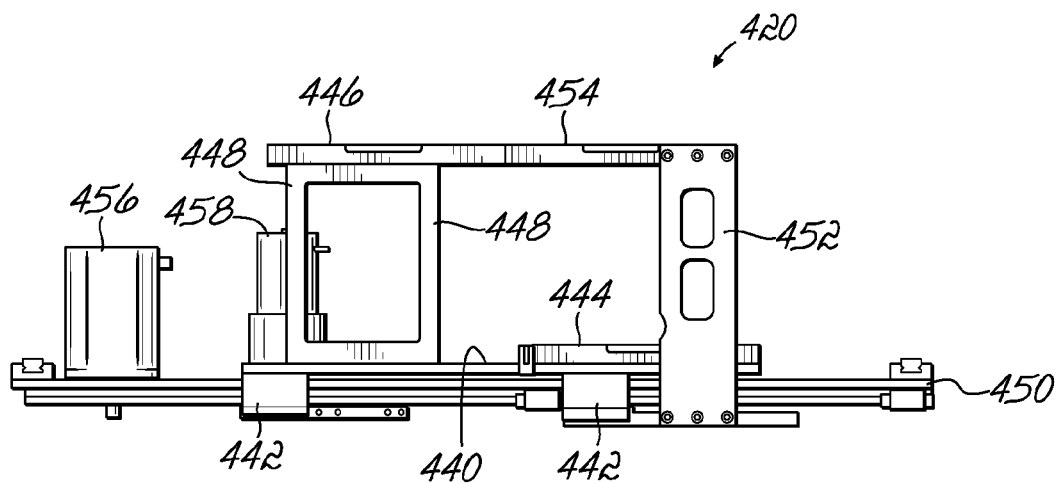
FIG. 25B is a side elevational view of the adjustable stage as shown in FIG. 24A.
Figure 25C:
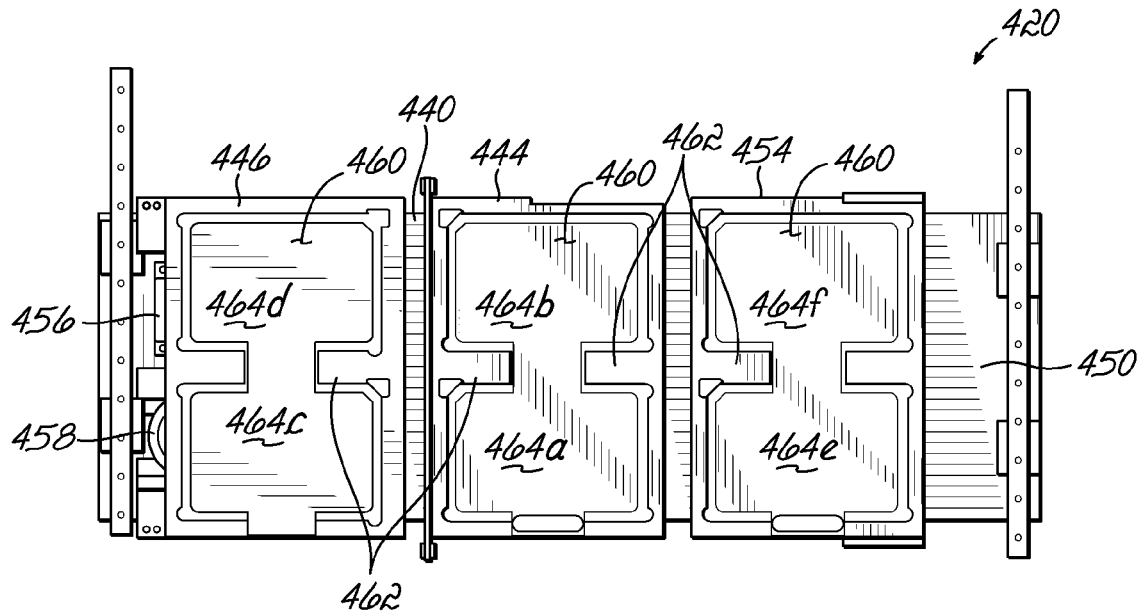
FIG. 25C is a top view of the adjustable stage as shown in FIG. 24B.
Figure 25D:
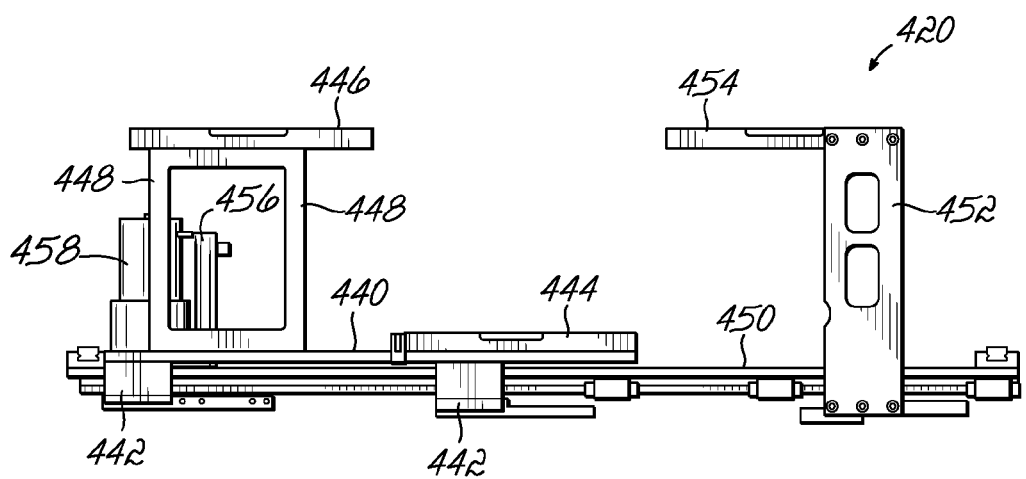
FIG. 25D is a side elevational view of the adjustable stage as shown in FIG. 24B.

Turning now to FIGS. 23A and 23B, the stage brace 384 may be configured to receive other embodiments of stages, such as the adjustable stage 420 (FIG. 24A), which allows the user to adjust the work space 52 (FIG. 1) in accordance with a particular need. In any event, a support hook 422, which is coupled to a stage, is configured to be coupled to a hook 418 of the stage brace 384. More particularly, the support hook 422 may be molded with an angled surface 424 that is keyed to match an angled opening 426 of the hook 418. A button 428 with a compression spring 430 are positioned within the stage brace 384, forward of the hook 418 and secured by a fixation device 432, for example, a bolt, screw, or other as is known.

In operation, the support hook 422, with the particular implemented stage embodiment, is directed downward to depress the button 428 and compress the spring 430. With the button 428 depressed, the stage hook 422 may then slide, in rearward-direction, to mate with the angled opening 426 of the hook 418. With the stage hook 422 positioned within the hook 418 of the stage brace 384, the compressive force from the button 428 onto the spring 430 is released. The spring 430 biases the button 428 upwardly, thereby locking the stage hook 422 relative to the hook 418.

In FIGS. 24A-25D, one embodiment of the adjustable stage 420 is described that allows the work space 54 (FIG. 1) within the lower housing 52 (FIG. 1) to be adaptable to support four trays 224 (FIG. 1) or six trays 224 (FIG. 1). In that regard, the adjustable stage 420 has a base 440 coupled to the bottom surface 382 (FIG. 21A) of the lower housing 52 (FIG. 1) by one or more legs 442. The base 440 supports a lower nest 444 that is adjacent to and spaced away from the bottom surface 382 (FIG. 21A) and a first upper nest 446 extending upwardly away from the base by way of two or more braces 448. A translating surface 450, longer than and slidably-coupled to the base 440, includes at least one brace 452 extending upwardly to a second upper nest 454.

The adjustable stage 420 further includes a first motor 456 that is operably coupled to the translating surface 450 so as to move the translating surface 450, and the associated second upper nest 454, in the x-direction. If desired, a second motor 458 is operably coupled to the lower nest 444 for translating the lower nest 444 simultaneously with the first and second upper nests 446, 454 in the x-direction. The motors 456, 458, while shown and described are not required and, instead, the nests 444, 446, 454 may be moved manually.

Each of the lower, first, and second upper nests 444, 446, 454 includes a tray supporting surface 460, with or without dividers 462, that are similar to the tray supporting surface 378 of FIG. 21A. As a result, the illustrative adjustable stage 420 has six tray supporting spaces 464a, 464b, 464c, 464d, 464e, 464f.

Figure 26:
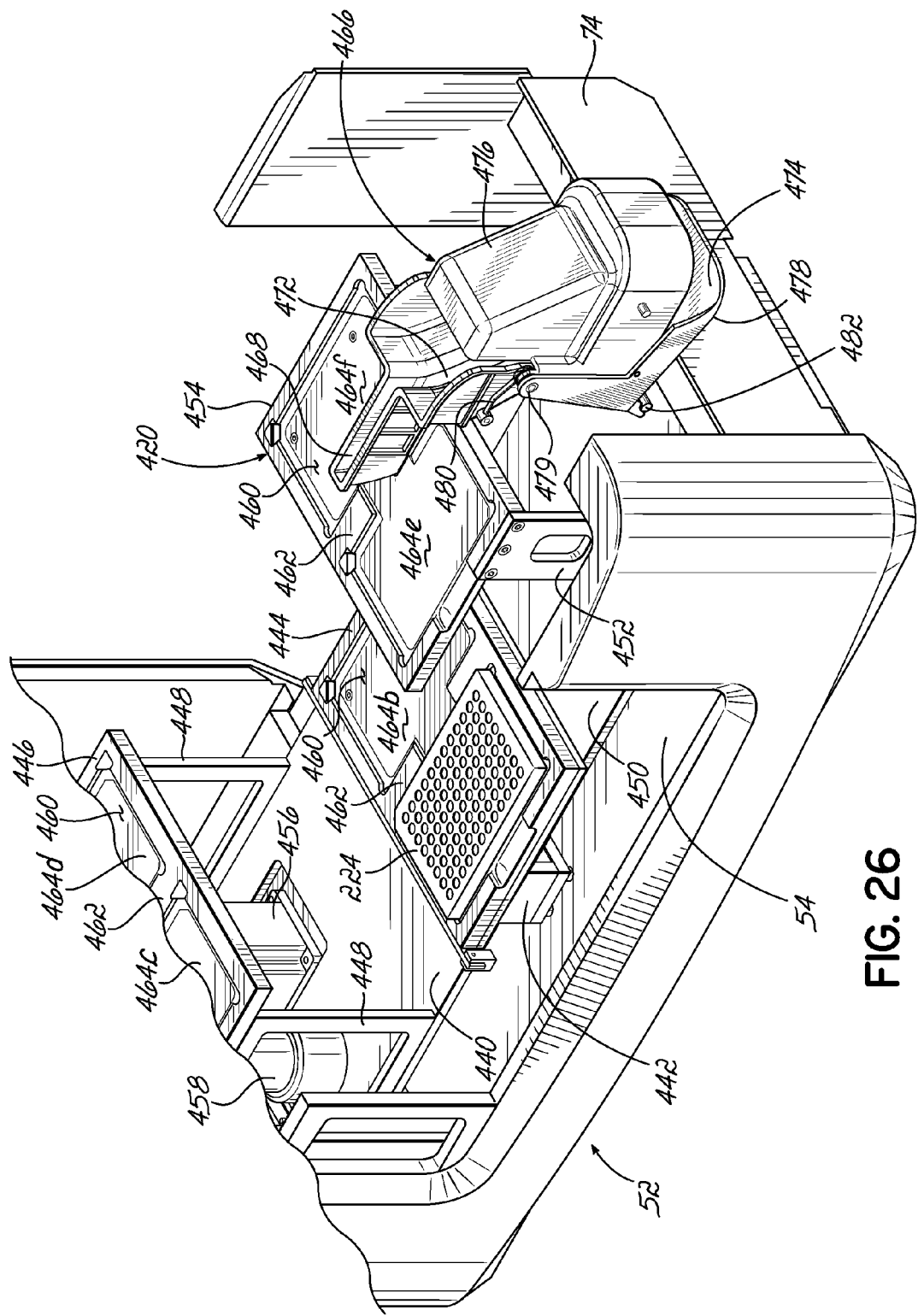
FIG. 26 is a perspective view of the adjustable stage with a tip ejection apparatus.

Turning now to FIG. 26, the second upper nest 454 may be configured to include an off-deck tip ejection apparatus 466 (though the ejection apparatus 466 is not limited to the second upper nest 454). The ejection apparatus 466 may be operably coupled to the second upper nest 454 at the divider 462 so that the second upper nest 454 may still receive one or two trays 224 in the tray spaces 464e, 464f.

Figure 28B:
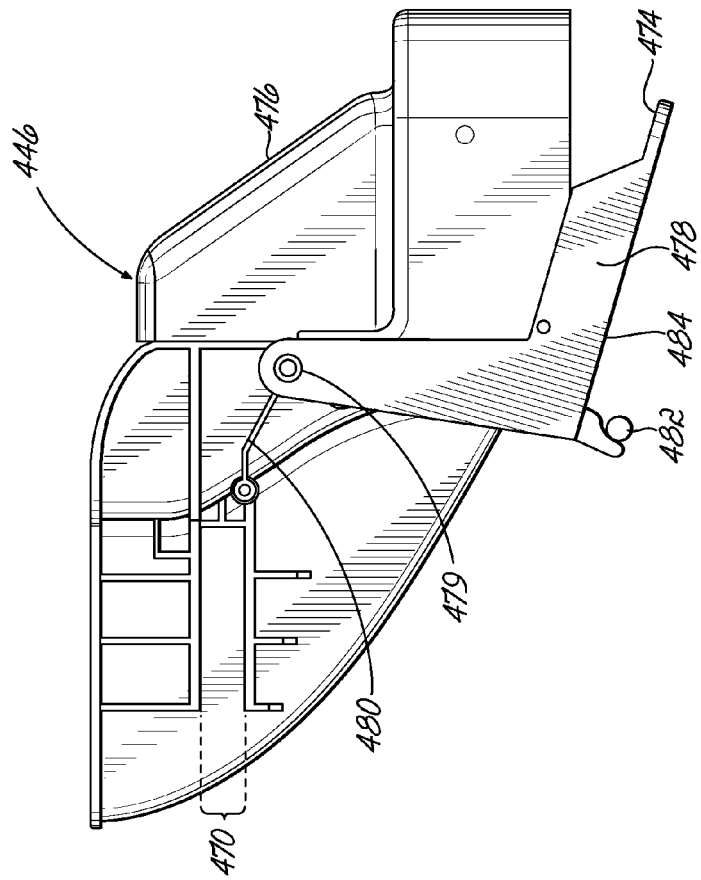
Figure 28A:
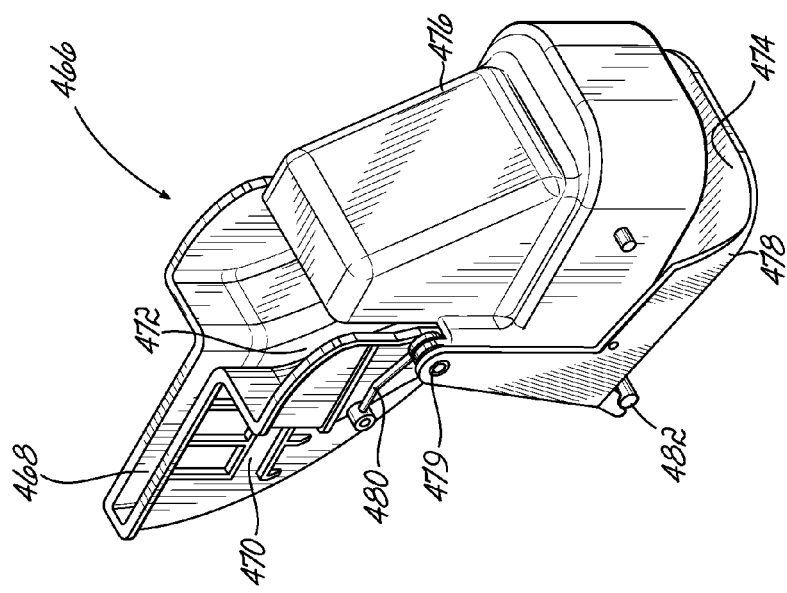

The ejection apparatus 466 is shown in greater detail in FIGS. 27A and 28A. In particular, the illustrated embodiment includes a tip receiving well 468 shaped to extend over the divider 462 (FIG. 26) as described above. For example, a gap 470 is shaped to receive the second upper nest 454 so that the tip receiving well 468 may extend, at least partially, over the second upper nest 454. The inner bottom surface 472 of the tip receiving well 468 may be sloped so that the tips 316a, 316b (FIG. 10) deposited therein are directed toward an ejection port 474. The tip receiving well 468 may expand laterally at a position that is adjacent to the ejection port 474 for providing a larger area in which to catch ejected tips 316a, 316b (FIG. 10).

The ejection port 474 includes a cover 476 and a rotatable mouth 478. The rotatable mouth 478 is operably coupled to the tip receiving well 468, at a point 479 that is near in the expanded portion, with a spring 480 biasing the mouth 478 toward the cover 476 and maintaining the ejection port 474 in a closed position (shown in FIG. 27B). While closed, the ejection port 474 accumulates used, disposable tips 316a, 316b (FIG. 10) from the pipetting head.

When the first motor 456 (FIG. 23) is operated to move the second upper nest 454 into close proximity to the sidewall 74 of the lower housing 52 (as shown in FIG. 26), an ejection rod 482, coupled to a lower outer surface 484 of the rotatable mouth 478, may engage the sidewall 74. With further operation of the first motor 456, the ejection rod 482 resists further translational movement of the rotatable mouth 478 while the tip receiving well 468 and the cover 476 continue to move. The rotatable mouth 478 rotates, against the bias of the spring, and opens the ejection port 474, as shown in FIGS. 28A and 28B. The pipette tips 316a, 316b (FIG. 10) may then fall out of the off-deck tip ejection apparatus 466 and into a suitable waste receptacle (not shown), or a recycling bin (not shown).

While not specifically illustrated here, one of ordinary skill in the art would readily appreciate that the automated liquid handling device 50 (FIG. 1) may be compatible with other conventional devices, such as the RAPIDSTAK, Orbitor, or Catalyst Express systems commercially-available from Thermo Fisher Scientific of Waltham, Mass., for the transfer of trays into and out of the automated liquid handling device; and devices for piercing, vacuum, washing, pumping, bar code reader, RFID reader, or stage thermal control. It would be appreciated by one of ordinary skill in the art that the automated liquid handling device 50 of FIG. 1 may include rotatable side panels 486 (FIG. 1) for providing accessibility to the work space 54 within the lower housing 52 from one or both sides of the automated liquid handling device 50.

While the present invention has been illustrated by a description of various embodiments, and while these embodiments have been described in some detail, they are not intended to restrict or in any way limit the scope of the disclosed invention. Additional advantages and modifications will readily appear to those skilled in the art. The various features of the present invention may be used alone or in any combination depending on the needs and preferences of the user. This has been a description of the present invention, along with methods of practicing the present invention as currently known.

What is claimed is:
1. An automated liquid handling device, comprising:
   a first housing portion;
   a second housing portion located above the first housing portion and having a rear wall;
   a vertically translatable support block supported by the second housing portion and being configured to vertically translate along the rear wall of the second housing portion;
   a drive mechanism configured to vertically translate the support block; and
   a liquid handling system supported within the second housing portion comprising:
      a housing;
      at least one pipetting head supported by the housing and being configured to aspirate and dispense a liquid; and
      an adaptor plate supported by the housing and configured to be releasably coupled to the support block so that the adaptor plate and the support block form a locking mechanism, the adaptor plate and the support block being configured for sliding vertical movement relative to each other and cooperating so as to releasably couple the adaptor plate to the support block in response to vertical sliding movement of the support block;

wherein the housing of the liquid handling system, including the at least one pipetting head supported by the housing, is vertically translatable with the support block when the adaptor plate is coupled to the support block.

2. The automated liquid handling device of claim 1, wherein the support block of the locking mechanism comprises:
a plunger that is moveable between an actuated position and a released position; and
a locking pin that is moveable between an extended position and a retracted position with respect to an outer surface of the support block, wherein when the locking pin is in the extended position, the support block may be operably coupled to or released from the adaptor plate, and when the locking pin is in the retracted position, the support block may be secured to the adaptor plate,
wherein moving the plunger from the retracted released position to the actuated position moves the locking pin from the retracted position to the extended position such that the support block may be received by or removed from the adaptor plate.

3. The automated liquid handling device of claim 1, wherein the at least one pipetting head includes a plunger mechanism operating with one or more fluid passages provided in the at least one pipetting head, the plunger mechanism being configured to aspirate or dispense the fluid from the one or more fluid passages.

4. The automated liquid handling device of claim 3, wherein the housing comprises a cage, the system further comprising:
a motor supported by the cage for actuating the plunger mechanism of the at least one pipetting head.

5. The automated liquid handling device of claim 4, wherein the at least one pipetting head is a matrix-style pipetting head comprising a plurality of fluid passages arranged in a two-dimensional array and the plunger mechanism comprises a plunger plate configured to interface the motor with the matrix-style pipetting head.

6. The automated liquid handling device of claim 5 further comprising an actuating mechanism configured to engage the plunger mechanism, wherein the actuating mechanism includes a locking clip to secure and release the matrix-style pipetting head with the cage.

7. The automated liquid handling device of claim 6, wherein the cage includes a magazine clip and a magazine of pipetting tips, the magazine clip further comprising:
at least two arms configured to receive the magazine of pipetting tips;
at least two slots into which a respective one of the at least two arms slide when receiving the magazine of pipetting tips; and
a biased locking device engaging the at least two arms and resisting removal of the at least two arms from the magazine clip when the magazine of pipetting tips is removed from the magazine clip.

8. The automated liquid handling device of claim 7, wherein the magazine clip further comprises:
a sensor configured transmit a signal in response to the relative position of the magazine of pipetting tips within the magazine clip; and
a controller operably coupled to the sensor and configured to control the motor in response to the signal.

9. The automated liquid handling device of claim 3, wherein the at least one pipetting head is an array-style pipetting head having a plurality of fluid passages arranged in a linear array, the liquid handling system further comprising:
a pipettor block operably coupled to the array-style pipetting head; and
a motor operably coupled to the array-style pipetting head for actuating the plunger mechanism.

10. The automated liquid handling device of claim 9, wherein the motor is further configured to move the pipettor block with the array-style pipetting head in at least one of an x-direction and a y-direction.

11. The automated liquid handling device of claim 9, wherein the pipettor block includes a crash prevention device to transmit a signal to the motor to prevent the array-style pipetting head from crashing into at least one vessel, the crash prevention device comprising:
a support housing;
a ring having a first position adjacent the support housing and a second position biased away from the support housing, the ring operably coupled to the array-style pipetting head; and
a motor switch, a microswitch, or a sensor positioned to be contacted by the ring when the ring is in the second position,
wherein a downward force applied to the array-style pipetting head by the motor creates an upward force on the ring by the array-style pipetting head and the signal terminates operation of the motor.

12. The automated liquid handling device of claim 9, wherein the pipettor block includes an ejector plate configured to eject the array-style pipetting head from the pipettor block.

13. The automated liquid handling device of claim 1, further comprising:
at least one vessel for supplying or receiving the liquid from the at least one pipetting head.

14. The automated liquid handling device of claim 13, further comprising:
a stage configured to support the at least one vessel.

15. The automated liquid handling device of claim 14, wherein the stage includes a plurality of moveable tray support surfaces.

16. The automated liquid handling device of claim 15, wherein at least one of the plurality of moveable tray support surfaces is positioned above the other ones of the plurality of moveable tray support surfaces.

17. The automated liquid handling device of claim 1, further comprising:
a tip ejection apparatus including a tip receiving well and an ejection port, the ejection port positioned and configured to release collected disposable tips outside of the automated liquid handling device.

18. The automated liquid handling device of claim 17, wherein the tip ejection apparatus is operably coupled to a moveable stage positioned within the automated liquid handling device, the moveable stage configured to move the tip ejection apparatus to a sidewall of the automated liquid handling device before releasing the collected disposable tips.

19. The automated liquid handling device of claim 1, wherein the first housing portion includes at least one moveable sidewall having a closed position that encloses a workspace therein and an open position configured to interface the first housing portion with a labware device that is external to the automated liquid handling device.

20. The automated liquid handling device of claim 2 wherein the locking mechanism further comprises:

a plurality of rails on the support block, proximate to the locking pin; and a corresponding plurality of grooves on the adaptor plate, wherein the plurality of rails are received by the corresponding plurality of grooves for aligning the adaptor plate with the support block when the support block is received by the adaptor plate.

21. The automated liquid handling device of claim 2, wherein the plunger is positioned in a first bore within the support block and the locking pin is positioned in a second bore within the support block, the first bore being generally orthogonal to the second bore, the plunger and the locking pin having corresponding angled surfaces such that a first movement by the plunger is translated to second movement, orthogonal to the first movement, by the locking pin.

* * * * *

UNITED STATES PATENT AND TRADEMARK OFFICE
CERTIFICATE OF CORRECTION

PATENT NO. : 9,696,332 B2
APPLICATION NO. : 13/188518
DATED : July 4, 2017
INVENTOR(S) : Brutler et al.

It is certified that error appears in the above-identified patent and that said Letters Patent is hereby corrected as shown below:

On the Title Page

Item (57) Abstract, Line 11, change "The support block is then, in turn, is configured" to --The support block is then, in turn, configured--.

In the Specification

In Column 1, Line 32, change "preparation system that adaptable to" to --preparation system adaptable to--.

In Column 1, Line 34, change "other sample handling systems and to grow with" to --other sample handling systems and grow with--.

In Column 1, Line 53, change "each having a one or more fluid" to --each having one or more fluid--.

In Column 2, Line 32, change "includes a plurality of workable surface," to --includes a plurality of workable surfaces,--.

In Column 3, Line 10, change "illustrating vertical translation the support block" to --illustrating vertical translation of the support block--.

In Column 3, Line 43, change "FIGS. 18B and 19B are cross-sectional view through" to --FIGS. 18B and 19B are cross-sectional views through--.

In Column 5, Line 13, change "so as to capture two plunger springs (only one spring 114) is shown between the top arms" to --so as to capture two plunger springs (only one spring 114 is shown) between the top arms--.

In Column 5, Line 18, change "operation of the plunger 98 and locking pin 94 are shown" to --operation of the plunger 98 and locking pin 94 is shown--.

Signed and Sealed this
Seventeenth Day of October, 2017

Joseph Matal
*Performing the Functions and Duties of the
Under Secretary of Commerce for Intellectual Property and
Director of the United States Patent and Trademark Office*

In Column 5, Line 22, change "As the plunger 98 moves downward until the bottom surface 112" to --As the plunger 98 moves downward, the bottom surface 112--.

In Column 10, Line 18, change "Turning now to FIG. 16, where one exemplary embodiment" to --Turning now to FIG. 16, one exemplary embodiment--.

In Column 10, Line 37, change "One exemplary dispenser mechanism, such as the plunger described in" to --One exemplary dispenser mechanism, such as the plunger, is described in--.

In Column 12, Line 64, change "A button 428 with a compression spring 430 are positioned" to --A button 428 with a compression spring 430 is positioned--.

In the Claims

In Claim 8, Column 15, Line 61, change "a sensor configured transmit a signal" to --a sensor configured to transmit a signal--.